US006436231B1

United States Patent
Graef et al.

(10) Patent No.: US 6,436,231 B1
(45) Date of Patent: *Aug. 20, 2002

(54) METHOD AND APPARATUS FOR CROSSLINKING INDIVIDUALIZED CELLULOSE FIBERS

(75) Inventors: Peter A. Graef, Tacoma; Colin Elston, Gig Harbor; Fred E. Olmstead, Tacoma; Clifford R. Bolstad, Milton; Mark W. Bowns, Auburn; Frank R. Hunter, Bellevue; Allan R. Carney, Puyallup, all of WA (US)

(73) Assignee: Weyerhaeuser, Federal Way, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/509,401

(22) Filed: Jul. 31, 1995

Related U.S. Application Data

(60) Division of application No. 07/820,323, filed on Jan. 13, 1992, now Pat. No. 5,437,418, and a continuation-in-part of application No. 07/665,761, filed on Mar. 7, 1991, now Pat. No. 5,252,275, and a continuation-in-part of application No. 07/607,268, filed on Oct. 31, 1990, now abandoned, which is a continuation-in-part of application No. 07/395,208, filed on Aug. 17, 1989, now Pat. No. 5,225,047, which is a continuation-in-part of application No. 07/284,885, filed on Dec. 15, 1988, now abandoned, which is a continuation-in-part of application No. 07/140,922, filed on Dec. 28, 1987, now abandoned, which is a continuation-in-part of application No. 07/004,729, filed on Jan. 20, 1987, now abandoned.

(51) Int. Cl.[7] .................................................. D21C 9/00
(52) U.S. Cl. .......................................... 162/9; 162/146
(58) Field of Search .......................... 162/9, 100, 157.6, 162/182, 184, 201, 146; 264/128, 122; 428/373; 241/28

(56) References Cited

U.S. PATENT DOCUMENTS 2,152,901 A 4/1939 Manning .................... 154/33

(List continued on next page.)

FOREIGN PATENT DOCUMENTS

| AU | B-59206/80 | 6/1983 |
| CA | 806352 | 2/1969 |
| DE | 27 13 300 | 10/1978 |

(List continued on next page.)

OTHER PUBLICATIONS

Van Verst, et al., Amine–Induced Lossen Rearrangements of 3–Hydroxy–5, 6–dihydrodouracil and N–Hydroxysuccinimide Benzenesulfonates, Journal of Heterocyclic Chemistry, vol. 16, (1979) p. 1329.

(List continued on next page.)

Primary Examiner—Brenda A. Lamb

(57) ABSTRACT

An apparatus is disclosed for preparing a quantity of individual treated fibers from one or more fiber mats. The apparatus comprises a fiber treatment zone, and a conveyor for conveying each mat through the fiber treatment zone. In the treatment zone each mat is impregnated by an applicator with a treatment material, such as a crosslinking substance, and conveyed directly to an attrition device. The attrition device fiberizes the mats to form a fiber output having a low nit level, such as no more than about three, and a dryer both dries the fiber output and cures the crosslinking substance. The fiberizer is configured to minimize the accumulation of fiber at locations therein. Fiber is transported from the attrition device to the dryer at a high velocity under reduced pressure to promote drying. A heated retention bin is provided after drying to increase curing time in the system. A thermobonding agent may be added to the dried and cured fibers to enhance the wet strength of webs made from the fiber.

24 Claims, 8 Drawing Sheets

U.S. PATENT DOCUMENTS

| | | | |
|---|---|---|---|
| 2,596,015 A | 5/1952 | Dunwody | 241/28 X |
| 3,136,649 A | 6/1964 | Keahey, Jr. | 117/4 |
| 3,208,676 A | 9/1965 | Jensen | 241/195 |
| 3,224,926 A | 12/1965 | Bernardin | 162/146 |
| 3,395,708 A | 8/1968 | Hervey et al. | 128/284 |
| 3,440,135 A | 4/1969 | Chung | 162/157 |
| 3,482,788 A | 12/1969 | Newell | 241/69 |
| 3,519,211 A | 7/1970 | Sakulich et al. | 241/18 |
| 3,554,862 A | 1/1971 | Hervey et al. | 162/158 |
| 3,637,146 A | 1/1972 | Banks | 241/194 |
| 3,658,613 A | 4/1972 | Steiger | 156/153 |
| 3,677,886 A | 7/1972 | Forssbald et al. | 162/72 |
| 3,750,962 A | 8/1973 | Morgan | 241/18 |
| 3,765,971 A | 10/1973 | Fleissner | 156/62.2 |
| 3,819,470 A | 6/1974 | Shaw et al. | 162/157 |
| 3,825,194 A | 7/1974 | Buehl | 241/191 |
| 3,901,236 A | 8/1975 | Assarsson et al. | 128/284 |
| 3,932,209 A * | 1/1976 | Chatterjee | 162/146 |
| 3,950,218 A | 4/1976 | Levesque | 162/201 |
| 3,950,219 A | 4/1976 | Levesque | 162/201 |
| 3,966,126 A | 6/1976 | Werner | 241/28 |
| 3,973,291 A | 8/1976 | Kolbach | 19/148 |
| 3,987,968 A | 10/1976 | Moore et al. | 241/28 |
| 4,035,219 A | 7/1977 | Cumbers | 156/290 |
| 4,144,122 A | 3/1979 | Emanuelsson et al. | 162/158 |
| 4,204,054 A * | 5/1980 | Lesag et al. | 162/146 |
| 4,241,881 A | 12/1980 | Laumer | 241/28 |
| 4,252,279 A | 2/1981 | Johansson et al. | 241/27 |
| 4,303,471 A | 12/1981 | Laursen | 162/158 |
| 4,351,699 A | 9/1982 | Osborn, III | 162/112 |
| 4,406,415 A | 9/1983 | Greer | 241/194 |
| 4,476,323 A | 10/1984 | Hellsten et al. | 564/294 |
| 4,533,507 A | 8/1985 | Tao | 261/153 |
| 4,572,440 A | 2/1986 | Tao | 241/23 |
| 4,600,462 A | 7/1986 | Watt | 156/278 |
| 4,650,127 A | 3/1987 | Radwanski et al. | 241/28 |
| 4,729,371 A | 3/1988 | Krueger et al. | 128/206.19 |
| 4,729,516 A | 3/1988 | Williams, Jr. | 241/189 R X |
| 4,767,499 A | 8/1988 | Simonsen et al. | 162/25 |
| 4,822,453 A | 4/1989 | Dean et al. | 162/157 |
| 4,853,086 A | 8/1989 | Graef | 162/157 |
| 4,889,595 A | 12/1989 | Herron et al. | 162/157 |
| 4,935,022 A | 6/1990 | Lash et al. | 604/368 |
| 5,022,964 A | 6/1991 | Crane et al. | 162/146 |
| 5,028,299 A | 7/1991 | Guidat et al. | 241/28 X |
| 5,041,104 A | 8/1991 | Seal | 604/367 |
| 5,137,537 A | 8/1992 | Herron et al. | 8/120 |
| 5,183,707 A | 2/1993 | Herron et al. | 428/364 |
| 5,190,563 A | 3/1993 | Herron et al. | 8/120 |
| 5,253,815 A * | 10/1993 | Bowns et al. | |

FOREIGN PATENT DOCUMENTS

| | | |
|---|---|---|
| DE | 29 02 457 | 7/1980 |
| DE | 1591 48 | 2/1983 |
| EP | 0 225 940 | 12/1985 |
| EP | 0 294 137 | 12/1988 |
| EP | 0 340 763 | 8/1989 |
| EP | 0 399 564 | 5/1990 |
| EP | 0 427 316 A2 | 5/1991 |
| EP | 0 427 317 A2 | 5/1991 |
| EP | 0 429 112 A2 | 5/1991 |
| EP | 0 440 472 A1 | 8/1991 |
| NO | 93769 | 1/1954 |
| SU | 950432 | 8/1982 |
| WO | WO84/00904 | 3/1984 |
| WO | WO9208843 | 5/1992 |

OTHER PUBLICATIONS

American Society of Agricultural Engineers, ASAE publication 10–81, *Forest Regeneration*, 108–117, (Mar. 1981).

HBA, Weyerhaeuser Paper Company, 1990.

Textile Fibers, Hoechst Celanese Corporation Catalog, Mar. 1991.

Marcher, Tailor–made Polyproplene and Bicomponent Fibers for the Nonwovens Industry, TAPPI Journal, Dec. 1991.

Barker, Polyester Fiber for Thermal Bonding Nonwovens, Eastman Chemical Products, Inc.

Thermal Bonding of Nonwovens by Means of Copolyester Melt Adhesive Fibers.

* cited by examiner

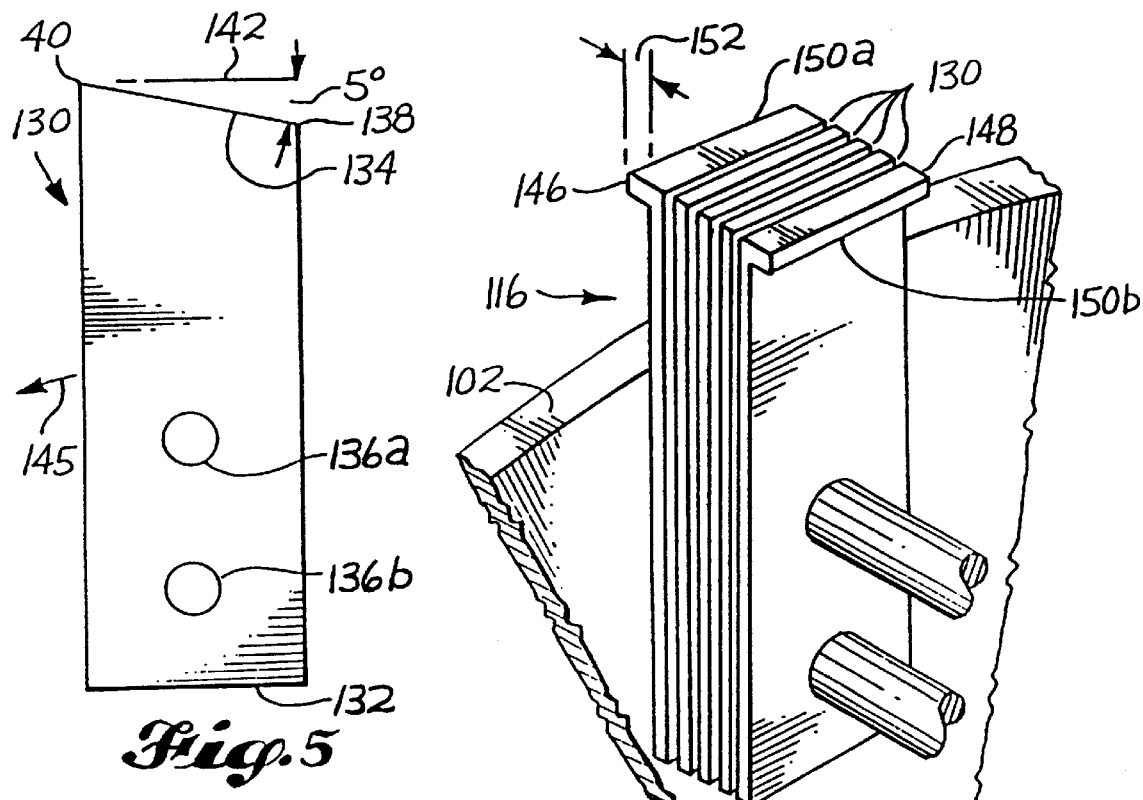
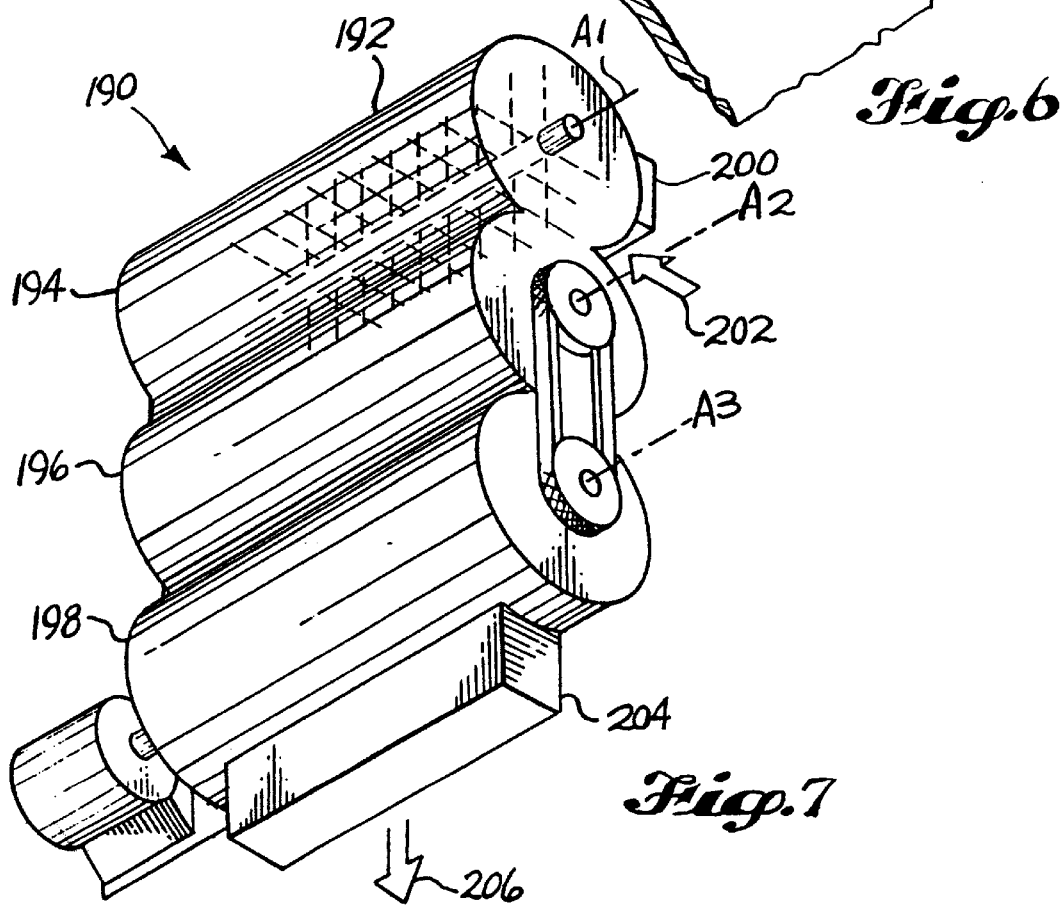

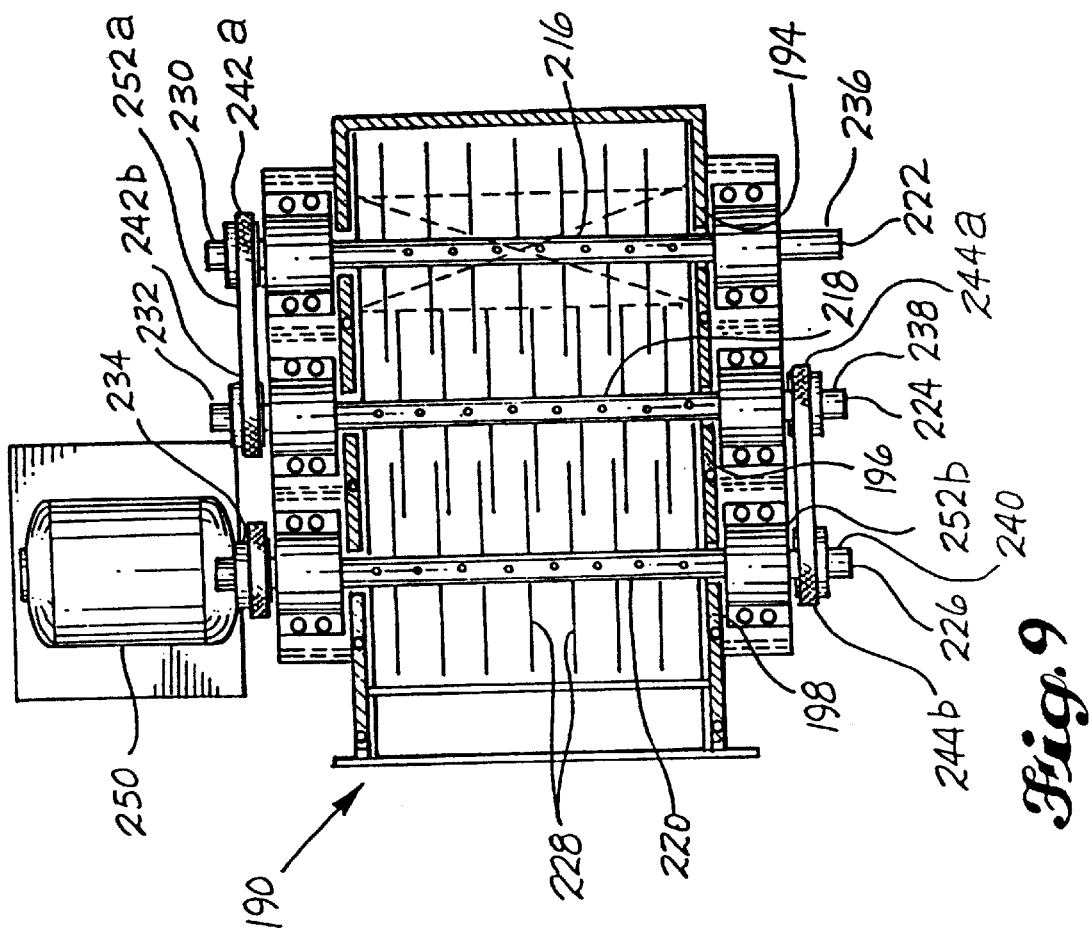
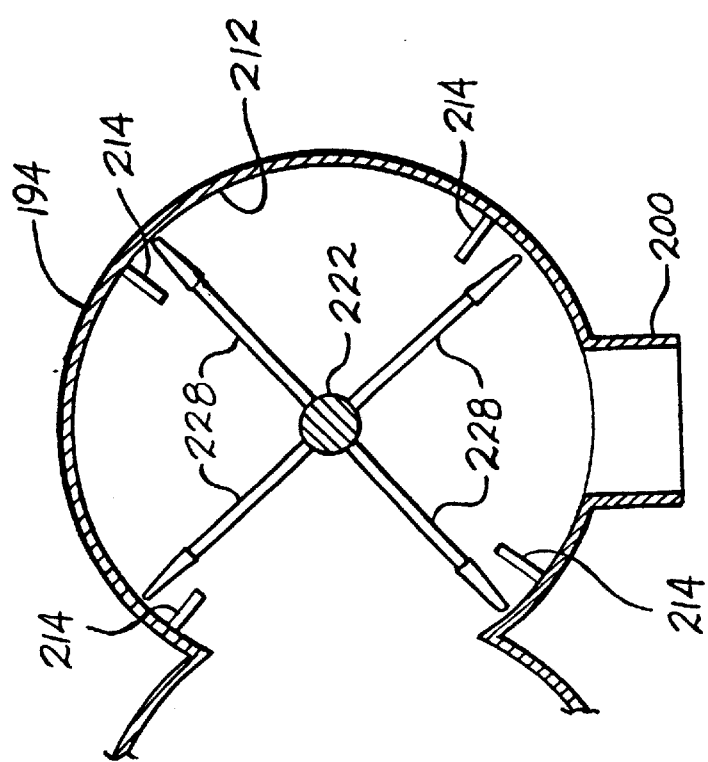
Fig. 9
Fig. 8

METHOD AND APPARATUS FOR CROSSLINKING INDIVIDUALIZED CELLULOSE FIBERS

This application is a continuation of application Ser. No. 07/820,323, filed Jan. 13, 1992 now U.S. Pat. No. 5,437,418.

CROSS-REFERENCE TO RELATED CASES

This is continuation-in-part of pending United States patent applications Ser. No. 07/665,761, filed Mar. 7, 1991 now U.S. Pat. No. 5,252,275; and Ser. No. 07/607,268, filed Oct. 31, 1990 abandoned, which is a continuation-in-part of Ser. No. 07/395,208, filed Aug. 17, 1989 now 5,225,047, which is a continuation-in-part of application Ser. No. 07/284,885, filed Dec. 15, 1998 abandoned, which is a continuation-in-part of application Ser. No. 07/140,922, filed Dec. 28, 1987 abandoned, which is a continuation-in-part of application Ser. No. 07/004,729, filed Jan. 20, 1987 abandoned.

BACKGROUND OF THE INVENTION

1. Field of the Invention

This invention relates to a fiber treatment apparatus and more particularly to the apparatus of the type which utilizes sprayers or other applicators to treat a fiber mat and mechanisms for subsequently fiberizing the mat following such treatment.

2. General Discussion of the Background

Various devices are known in the art for treating fibers with crosslinking agents in mat form and thereafter breaking the mats into individual fibers. For example, U.S. Pat. No. 3,440,135 to Chung discloses a mechanism for applying a crosslinking agent to a cellulosic fiber mat, then passing the mat while still wet and following "aging," through a fiberizer, such as a hammermill to fiberize the mat, and drying the resulting loose fibers in a two stage dryer. The first dryer stage is at a temperature sufficient to flash water vapor from the fibers and the second dryer stage is at a temperature that effects curing of the crosslinking agent. A cyclone separator is then illustrated separating the fibers from the gas and for subsequent collection. Chung mentions the need for the "aging" step, of many hours duration, in order to reduce the level of nits in the resulting fiber product. As described below, nits are typically interbonded fibers which can interfere with product quality. Therefore, the Chung apparatus suffers from the drawback of requiring the inconvenient and costly storage of wet fiber mats (e.g. in roll form) for a substantial period of time in order to minimize nit formation.

Unfortunately, fiberization processes known in the art which employ currently available fiberizing or comminution machinery yield crosslinked fibers that have too many nits and knots to be acceptable for many uses. A probable reason is that such machinery has excess dead space where fibers are excessively pressed together and/or has localized regions of elevated temperature hot enough to cause premature curing of the crosslinking agent while fibers are in intimate contact with each other. Since fiberization is performed on a mat that is still wet with the uncured crosslinking agent, dead spaces and hot spots in the fiberizer would encourage the formation of interfiber bonds, which form nits, that virtually cannot be broken by downstream equipment.

Interfiber bonding in a conventional fiberizer apparatus can also lead to production of excessive amounts of "fines," which are undesirably short fibers due principally to fiber breakage. Crosslinking imparts substantial brittleness to cellulose fibers, which thereby exhibit limited compliance to mechanical stresses. Nits are especially susceptible to mechanical stresses because of their density which is much greater than the density of individual fibers. Excess fiber breakage and fines not only degrade absorbency but can substantially reduce the loft and resiliency of a product made from crosslinked fibers.

One approach to reducing fines is to diminish interfiber crosslinking, as in published European Patent Application Nos. 427,316 A2; 429,112 A2; 427,317 A2; and 440,472 A1, as well as in copending United States patent application Ser. No. 07/607,268, filed Oct. 31, 1990. A drawback to this approach is that the substantial elimination of interfiber bonds produces a web having low tensile strength. Wet laid sheets made from such fibers tend to fall apart, and are unsuitable for many industrial applications.

Yet another problem with prior processes is that output from the system is so rapid that fibers treated with the crosslinking agent do not have sufficient time to cure after they are fiberized and dried. Curing time can be increased by lengthening the conduit through which fiberized and dried material passes, but such a solution is expensive. Lengthening conduits requires a large capital investment that reduces cost efficiency.

Hence, there is a need for an apparatus that will produce treated fibers, such as intrafiber crosslinked cellulose, having a nit level lower than levels obtainable with existing equipment. There is also a need for such an apparatus that will produce fibers from a mat comprised of crosslinked cellulose while not causing significant breakage of individual fibers of the mat.

It is an object of this invention to provide such an individualized, intrafiber crosslinked cellulose web that has improved wet tensile strength.

It is another object of the invention to provide a process for producing an individualized, intrafiber crosslinked product that provides increased curing time for crosslinking to progress after the fibers are dried.

It is yet another object of the invention to provide such a process that has improved flash drying of moisture from the fibers prior to curing.

It is another object of the invention to enhance the uniformity of crosslinking agent application to a fibrous mat.

Another object of the present invention is to provide an apparatus and method for producing treated fibers, such as crosslinked cellulose fibers, with a low nit level and preferably a nit level no greater than about three.

Another object is to provide such an apparatus and method that comminutes one or more mats of non-crosslinked cellulose fibers which have been impregnated with a crosslinking substance, where the comminution is performed before the crosslinking substance is dried and cured.

Another object is to provide such an apparatus and method that minimizes the breakage of individual fibers.

Another object is to provide such an apparatus and method that yields crosslinked fibers having substantially no knots.

It is yet another object to provide a crosslinking process that operates at a pH that is compatible with standard unmodified papermaking equipment.

Finally, it is an object of the present invention to provide a sheet having high bulk wet resilience and good porosity into which liquid impregnants can be efficiently introduced.

These and other objects of the invention will be understood more clearly by reference to the following detailed description and drawings.

SUMMARY OF THE INVENTION

The apparatus of the present invention is particularly adapted for preparing a quantity of individual crosslinked cellulose fibers from one or more mats comprised of non-crosslinked cellulose fibers. The apparatus comprises: an applicator that applies a crosslinking substance to a mat of cellulose fibers at a fiber treatment zone; a fiberizer having a fiberizer inlet; a conveyor that conveys the mat through the fiber treatment zone and directly to the fiberizer inlet without stopping for curing. The fiberizer provides sufficient hammering force to separate the cellulose fibers of the mat into a fiber output of substantially unbroken individual cellulose fibers. A dryer coupled to the fiberizer receives the fiber output, dries the fiber output, and cures the crosslinking substance, thereby forming dried and cured fibers. The fiberizer preferably fiberizes the treated mat to form a fiber output having a low nit level, such as a nit level of no more than about 3.

The apparatus also includes a reduced pressure conduit between the fiberizer and dryer in which the individual cellulose fibers are heated and the velocity of their flow is increased after they leave the fiberizer. This conduit opens into an expansion chamber that allows the fiber flow to expand and increase fiber separation. The flow velocity of the fibers in the conduit is preferably increased by reducing the diameter of the conduit between the fiberizer and dryer. A downstream connection between the conduit and dryer gradually increases in diameter to provide an expansion zone between the conduit and expansion chamber. The reduced diameter conduit provides an area of reduced pressure that promotes evaporation of moisture from the fibers of the conduit. The expansion chamber subsequently provides another evaporation zone in which moisture is quickly and explosively released from the fibers, thereby further enhancing their separation and production of individualized fibers.

The apparatus further includes a hot air blower that blows hot air into the conduit toward the expansion chamber. Fibers are introduced into the conduit between the blower and expansion chamber through a fiber introduction inlet. The blower preferably introduces hot air at a temperature of about 260° C. into the conduit to transport the fibers and reduce their moisture content in the reduced pressure environment of the necked down conduit.

The apparatus also preferably includes a heated retention chamber into which dried, treated fiber output is introduced for a preselected period of time to allow curing of the crosslinking substance. In some embodiments, the retention chamber is positioned between the flash drying and curing chambers of the dryer. In other embodiments, the retention chamber is downstream from the curing chamber, for example, after a cyclone separator that separates fibers received from the curing chamber. In especially preferred embodiments, the retention chamber has the shape of an inverted pyramid with an open base through which the fibers are introduced. The apex of the pyramidal chamber can selectively be opened and closed to control the movement of cured fibers out of the bottom of the retention chamber.

Representative conveyors include, but are not limited to, conveyor belts and roller mechanisms. In the fiber treatment zone, the crosslinking substance can be applied to the mat via any suitable means including, but not limited to, spraying, roller coating, and a combination of spraying and roller coating. The applicator that applies the crosslinking agent is preferably a shower spray followed by an impregnation roller that presses the crosslinking substance into the mat. In especially preferred embodiments, the shower spray includes a pair of opposing shower spray applicators that direct droplets of the crosslinking agent toward the two opposing face of the mat. The impregnation roller is preferably a pair of opposing rollers that cooperatively exert 1–50 psi, preferably 1–2 psi, impregnation pressure on the mat. In particularly disclosed embodiments, the shower spray applicators are positioned vertically over a fiberizer inlet, and the impregnation rollers abut the mat between the spray applicators and the fiberizer outlet. The area between the rollers can form a flooded nip that diminishes flow of excess crosslinking agents into the fiberizer outlet.

The dryer of the apparatus preferably includes a drying zone for forming dried fibers, and a curing zone for curing the crosslinking substances on the dried fibers. The drying zone preferably includes the expansion chamber, which has an inlet for receiving the individual cellulose fibers from the restricted diameter conduit. The dryer inlet has a temperature within the range of about 200–315° C. so as to flash evaporate moisture from and expand the cellulose fibers. The subsequent curing zone has an outlet through which the dried and cured fibers are delivered from the dryer. The outlet of the curing zone preferably has a temperature within a range of about 140–180° C.

The drying and curing zones preferably comprise a first and a second tower, respectively, in which the fibers are lofted to ensure thorough fiber separation. In the dryer, flash drying of the fibers occurs which microscopically explosively separates fibers loosely adhering together in the form of a fiber knot.

The fiberizer apparatus comprises at least an attrition device which produces a low nit level fiber output. The fiberizer may also optionally include a disk refiner of conventional design coupled to the attrition device and a fluff generator of novel design coupled to the disk refiner.

A preferred embodiment of the attrition device comprises a substantially cylindrical rotor rotatable about a longitudinal axis and a housing surrounding the rotor. The housing may include up to six mat feeder assemblies each capable of simultaneously urging a wet or dry treated mat into engagement with the rotating rotor. The rotor includes groups or stacks of hammers extending longitudinally and radially over the surface of the rotor, such as in an alternating fashion. In a specific arrangement, any hammer group is longitudinally and radially adjacent an empty space large enough to accept a hammer group, and any said empty space is adjacent a hammer group. Air flow may be directed within the attrition device away from the ends and toward the center of the rotor therein to minimize the possible accumulation of fibers at such end locations. Also, the attrition device may include a fluid, and preferably a liquid, flushing mechanism for use in cleaning any accumulated fiber from the attrition device. The attrition device substantially lacks internal hot spots and dead spaces, thereby inhibiting formation of nits in the fibers produced by said device. Also, the attrition device inhibits fiber breakage.

A preferred embodiment of the fluff generator comprises three rotors having coplanar parallel longitudinal axes each surrounded by a cylindrical housing. The rotor housings are contiguous and partially intersecting. All three rotors rotate synchronously in the same direction about their axes. Each rotor comprises multiple longitudinally extended groups of multiple radially projecting pins which, during rotation of the rotor, travel past multiple, longitudinally extended groups of multiple shorter pins projecting from the inside of the corresponding rotor housing toward the rotor axis. The fluff generator is effective for providing additional comminution, if required, of the fibers, particularly of residual knots in the comminuted fibers produced by the attrition device.

The present invention also includes a method of producing crosslinked cellulose fibers by applying a crosslinking substance to a mat of cellulose fibers at a fiber treatment zone, then conveying the mat from the fiber treatment zone directly into a fiberizer without stopping to cure the crosslinking substance. The fiberizer separates the fibers by hammering them into substantially unbroken individual cellulose fibers, preferably having a nit level of no more than about 3. The separated fibers are then dried at a temperature of about 200–315° C. so as to flash evaporate water from the fiber output, and then cured at a temperature of about 140–180° C.

In particularly preferred embodiments, a thermobonding agent is added to the dried and cured cellulose fibers produced by the foregoing process. The mixture of thermobonding agent and cellulose fibers forms a mixture that is made into a web, and the web is then heated to a sufficient temperature to thermobond the fibers together and increase the wet strength of the web. The thermobonding agent can, for example, be a bicomponent fiber having a core component in a sheath, wherein the core component (for example, polypropylene) has a higher melting point than the sheath component (for example, polyethylene). The thermobonding agent comprises 5–50% by weight, more preferably 20–40% of the mixture. The thermobonded crosslinked fibers have been found to produce a bulky, crosslinked product having good absorbent properties.

When the core of the bicomponent fiber is made of polypropylene and the sheath is made of polyethylene, the mixture is heated to about 130–150° C. to melt the polyethylene sheath, while allowing the polypropylene core to maintain its structural integrity. The intact core provides a matrix in the mat that enhances the wet strength of the resulting web. The enhanced wet strength of the web permits formation of cellulose products using a wet laid process. These products may be impregnated with binders, such as carboxymethylcellulose. Soft, flexible packaging materials can be made by impregnating the product with a binder such as acrylic or vinyl acetate latex. Flame-retardant cellulose materials can be made by impregnating the mat with polyvinyl chloride or polyvinylidine chloride, for use as insulation material in buildings. Rigid packaging or soundproofing aterials can similarly be made by impregnating the wet laid mat with acrylic or polyvinylacetate binders.

In yet another embodiment, the dried and cured fibers of the present invention can be collected and introduced into a pulp furnish to increase bulk and subsequent impregnation of chemicals into a sheet made from the pulp furnish. The high bulk fibers of the present invention increase the porosity and absorbance of a sheet made from the furnish. Compared to a standard fiber made without addition of high bulk fibers, the pulp furnish of the present invention produces a sheet having an increased saturation rate, increased bulk, and under certain conditions enhanced strength at higher bulk. Enhanced absorbency of the resulting sheeted product increases impregnation efficiency and reduces waste during subsequent impregnation of the fibrous material with binders such as latex. In particularly preferred embodiments, the high bulk fibers of the present invention can be added to a pulp furnish, which is then used to make fibers that are subjected to the crosslinking process of the present invention.

The crosslinking agents of the present invention can include polycarboxylic acids and urea derivatives consisting of methylolated urea, methylolated cyclic ureas, lower alkyl substituted cyclic ureas, dihydroxy cyclic ureas, lower alkyl substituted cyclic ureas, and methylolated dihydroxy cyclic ureas; acid anhydrides from the group consisting of maleic anhydride, phthalic anhydride, 4-carboxyphthalic anhydride, pyromellitic anhydride, and mellitic anhydride, pyromellitic anhydride, and mellitic anhydride; polycarboxylic acids; dialdehydes; and mixtures thereof. The crosslinking agent is more preferably a polycarboxylic acid, for example a tricarboxylic or tetracarboxylic acid, such as citric acid (2-hydroxy-1,2,3-propanetricarboxylic acid) or 1,2,3,4-butanecarboxylic acid.

The pH of the cellulose fibers remains above about 2 after the crosslinking agent is applied to the mat, and is preferably no more than about 4. The most preferred pH range is 3–4. A pH below 2 may damage the cellulose fibers by acid hydrolysis, whereas a pH above 4 may reduce the efficiency of the crosslinking reaction.

BRIEF DESCRIPTION OF THE DRAWINGS

FIG. 5 is a plan view of a hammer plate used in the rotor of FIG. 4.

FIG. 6 is an isometric view of a stack of hammer plates used in the rotor of FIG. 4.

FIG. 7 is an isometric view of the exterior of a preferred embodiment of a fluff generator included as an option in the apparatus of the present invention.

FIG. 8 is a transverse sectional view through a housing portion and rotor of the fluff generator of FIG. 7.

FIG. 9 is a plan sectional view of the fluff generator of FIG. 7.

DETAILED DESCRIPTION

Overall System

Figure 1:
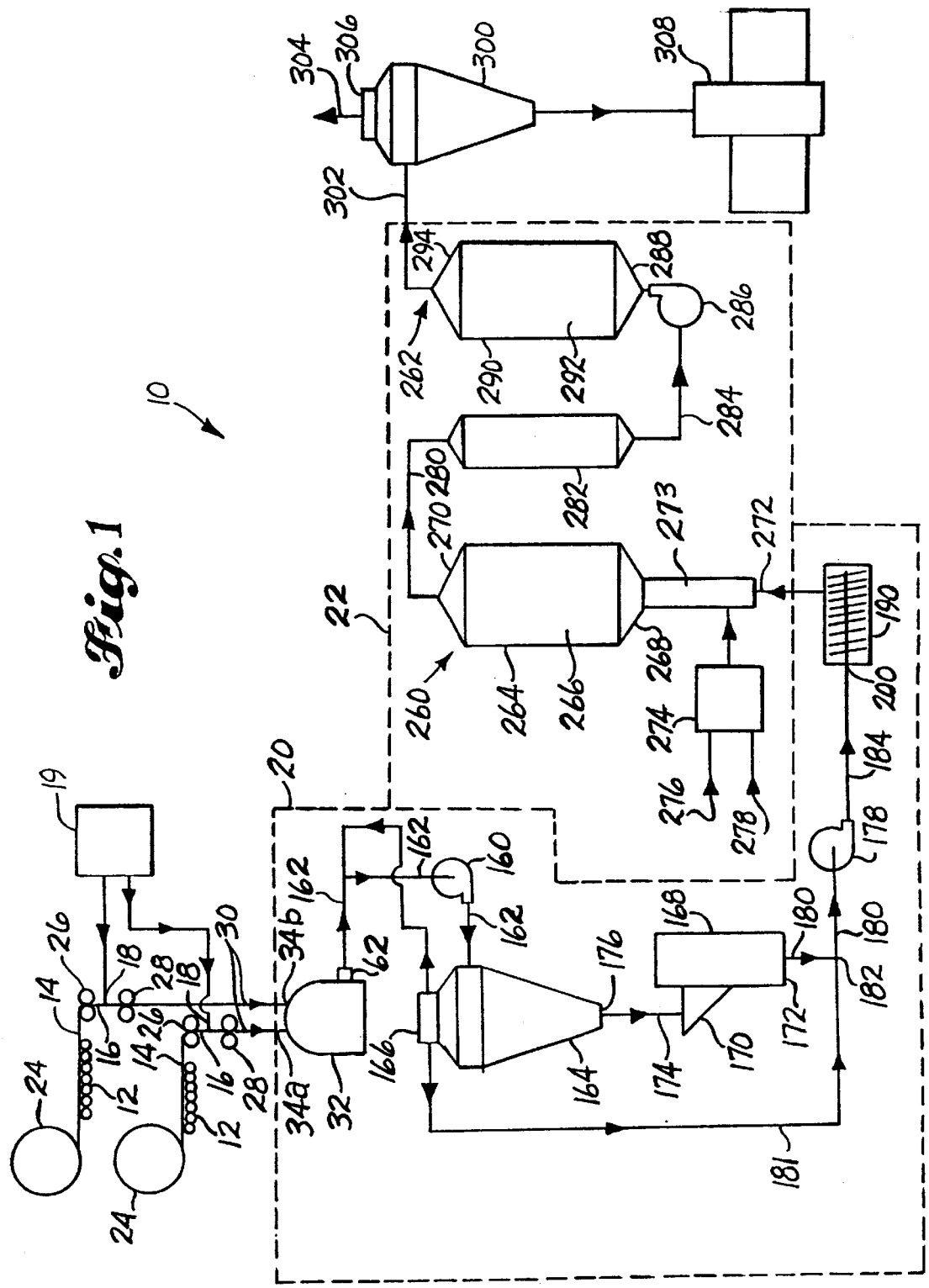
FIG. 1 is a schematic depiction of the components of the apparatus of the present invention.

The apparatus 10 (FIG. 1) of the present invention comprises a conveying device 12 for transporting a mat 14 of cellulose fibers or other fibers through a fiber treatment zone 16; an applicator 18 for applying a treatment substance such as a crosslinking substance from a source 19 thereof to the mat 14 at the fiber treatment zone 16; a novel type of fiberizer 20 for completely separating the individual cellulose fibers comprising the mat 14 to form a fiber output comprising substantially unbroken cellulose fibers substantially without nits or knots; and a dryer 22 coupled to the fiberizer for flash-evaporating residual moisture from the fiber output and for curing the crosslinking substance, thereby forming dried and cured cellulose fibers. The apparatus 10 of the present invention has been observed to consistently produce fibers with a nit level of less than three, which is substantially lower than obtainable using any apparatus presently known in the art.

Raw Materials

As used herein, a "mat" denotes any non-woven sheetlike structure comprising cellulose fibers or other fibers that are not covalently bonded together. The fibers may be obtained from wood pulp or other source including cotton "rag", hemp, grasses, cane, husks, cornstalks, or any other suitable source of cellulose fiber that can be laid into a sheet.

Preferably, the mat 14 includes a debonding agent which can be applied after formation of the mat 14 or added to cellulose fibers before forming the mat therefrom. For example, with mats comprising pulp fibers, the debonding agent can be added to wet pulp before the mat is laid using conventional papermaking machinery. Debonding agents tend to minimize interfiber bonds between fibers of the mat. A fair, but nonexhaustive, sampling of debonding agents is disclosed in U.S. Pat. Nos. 3,395,708 and 3,544,862 to Hervey, et al.; U.S. Pat. No. 4,144,122 to Emanuelsson, et al.; U.S. Pat. No. 3,677,886 to Forssblad, et al.; U.S. Pat. No. 4,351,699 to Osborne III; U.S. Pat. No. 4,476,323 to Hellsten, et al.; and U.S. Pat. No. 4,303,471 to Laursen, all of which are herein incorporated by reference. Any suitable debonding agents may be used, such as preferably Berocell 584 from Berol Chemicals, Incorporated of Metairie, Louisiana in a 0.25% weight of debonder to weight of fiber. However, use of a debonding agent is not required for complete fiberization using the present apparatus.

The mat 14 of cellulose fibers is preferably in an extended sheet form stored in the form of a roll 24 until use. While the mat 14 can also be one of a number of baled sheets (not shown) of discrete size, rolls 24 are generally more economically adaptable to a continuous process. The cellulose fibers in the mat 14 should be in a non-woven configuration produced by a pulping process or the like, such as in a paper mill, and can be bleached or unbleached. The mat 14 can have any of a wide variety of basis weights. For simplicity, FIG. 1 shows a roll 24 as the source of each mat 14, but it is to be understood that the mat 14 can be supplied in any form amenable for storing sheet-like structures. Also, the mat may be obtained directly from the headbox of paper making equipment or otherwise formed in any suitable manner.

It is normally not necessary that the cellulose fibers comprising the mat 14 be completely dry. Since cellulose is a hydrophilic substance, molecules thereof will typically have a certain level of residual moisture, even after air drying. The level of residual moisture is generally 10% w/w or less, which is not detectable as "wetness."

FIG. 1 also shows that more than one supply, such as multiple rolls 24, of the mat 14 of cellulosic fibers can be simultaneously processed using the present invention. For simplicity, FIG. 1 shows two rolls 24 being processed, but it is to be understood that even more supplies of cellulosic fibers can be simultaneously processed, depending upon the capacity of the equipment, particularly the fiberizer 20. As discussed herein below, the preferred embodiment of the fiberizer 20 can fiberize up to six mats at one time.

Figure 10:
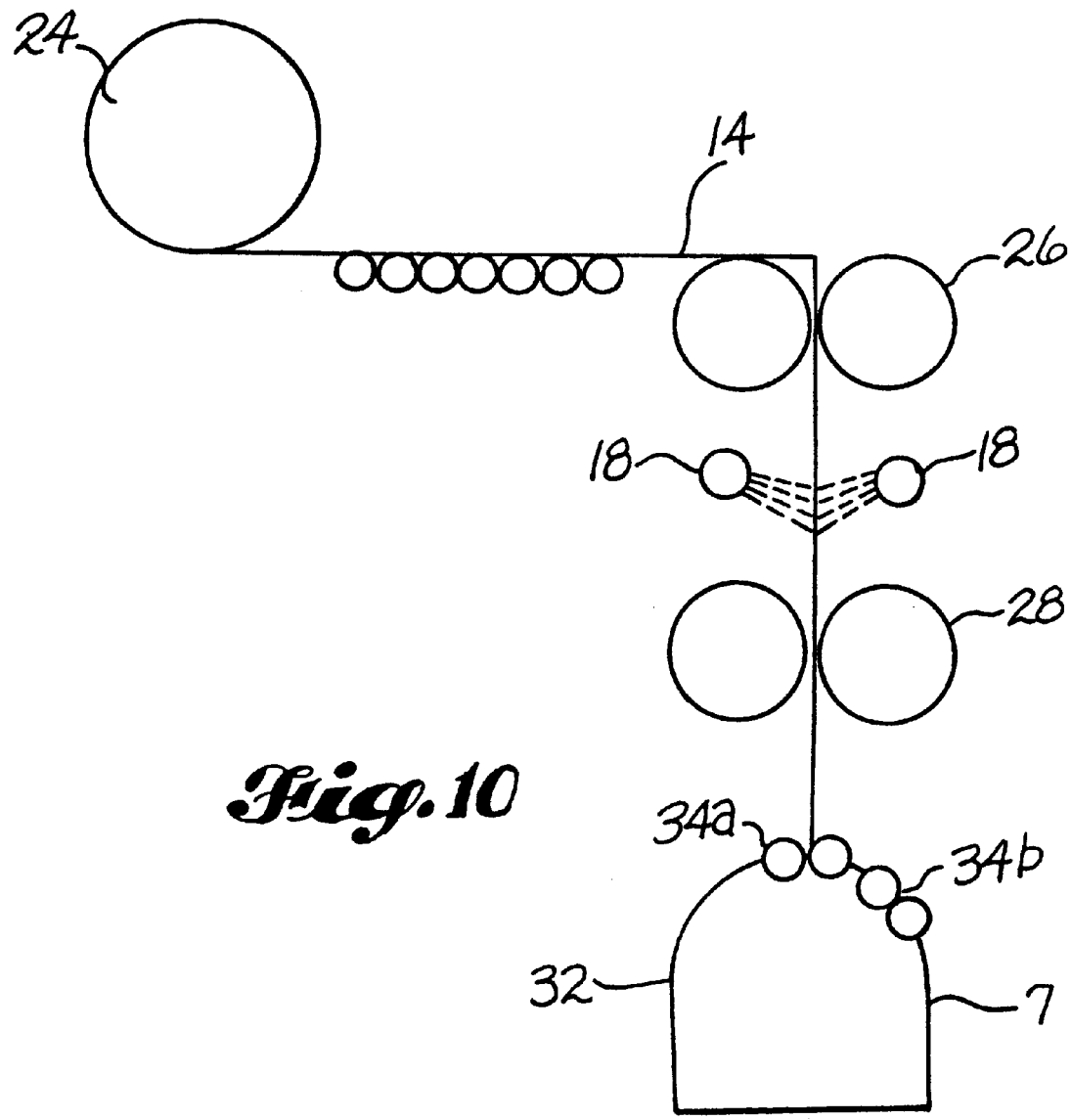
FIG. 10 is an enlarged view of the crosslinking applicator portion of the diagram of FIG. 1, only one feeder roll being shown for simplicity.

At the fiber treatment zone 16, sprayers or other applicators 18 apply chemicals such as crosslinking agents to the mat. Typically, chemicals are applied uniformly to both sides of the mat. FIG. 10 shows one particular embodiment of the applicator in which a pair of opposing sprayers 18 are positioned adjacent each face of mat 14 to spray crosslinking agent at the mat and saturate it with the crosslinking agent. The wetted mat passes between a pair of impregnation rollers 28 which assist in distributing the chemicals uniformly through the mat. Rolers 28 cooperatively apply light pressure on the mat (for example, 1–2 psi) to force crosslinking agents uniformly into the interior of the mat across its width. The rollers 28 form a seal with the mat such that the crosslinking agent can form a puddle at the nip. This seal helps prevent the liquid crosslinking agent from falling into the inlet 34a of the fiberizer 32 that is positioned vertically below the flooded nip. Other applicators may also, of course, be used. Examples of other applicators include size presses, nip presses, blade applicator systems and foam applicators.

Each mat 14 is urged by the first and second pair of rollers 26, 28 through the fiber treatment zone 16 where the mat 14 is impregnated with a liquid crosslinking substance. The crosslinking substance is preferably applied to one or both surfaces of the mat using any of a variety of methods known in the art useful for such a purpose, such as spraying, rolling, dipping, or an analogous method. Spraying has the advantage of consistent and rapid full coverage of a planar surface such as a mat at a controllable rate, especially when the spray is applied to a surface moving past a spray nozzle or analogous applicator at a fixed rate. Roller applicators have also proven to be reliable and effective in such applications as paper coating and the like and would therefore be effective for applying the crosslinking substance in the present instance. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

The rollers 28 can be positioned relative to each other to have a defined gap therebetween so as to enable them to impart a controlled squeeze action to the impregnated mat as it departs the fiber treatment zone 16. As mentioned above, such squeezing action facilitates complete and uniform penetration of the crosslinking substance throughout the thickness dimension of the mat. The squeezing action also helps to regulate the degree of saturation ("loading level") of the mat 14 with the crosslinking substance.

The crosslinking substance is a liquid solution containing any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

Preferred types of crosslinking substances are selected from the group consisting of urea derivatives such as methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; acid anhydrides from the group consisting of maleic anhydride, phthalic anhydride, 4-carboxyphthalic anhydride, pyromellitic anhydride, and mellitic anhydride; polycarboxylic acids; dialdehydes; and mixtures thereof. A specifically preferred crosslinking substance would be dimethyloldihydroxyethylene urea (DMDHEU). In addition, another preferred crosslinking agent is a polycarboxylic acid, such as citric acid (2-hydroxy-1,2,3-propanetricarboxylic acid) or the 1,2,3,4-butanecarboxylic acid disclosed in co-pending United States patent application Ser. No. 07/395,208 filed Aug. 17, 1989, which is a continuation-in-part of Ser. No. 07/284,885, filed Dec. 15, 1988, which is a continuation-in-part of Ser. No. 07/140,922, filed Dec. 28, 1987, which is a continuation-in-part of Ser. No. 07/004,729, filed Jan. 20, 1987. Other crosslinking materials are known in the art, such as described in the previously mentioned Chung patent; U.S. Pat. No. 4,935,022 to Lash et al.; U.S. Pat. No. 4,889,595, to Herron et al.; U.S. Pat. No. 3,819,470 to Shaw et al.; U.S. Pat. No. 3,658,613 to Steiger et al.; U.S. Pat. No. 4,822,453 to Dean et al.; and U.S. Pat. No. 4,853,086 to Graef et al., all of which are hereby incorporated herein by reference.

Suitable catalysts include acidic salts which can be useful when urea-based crosslinking substances are used. Such salts include ammonium chloride, annnonium sulfate, aluminum chloride, magnesium chloride, or mixtures of these or other similar compounds. Alkali metal salts of phosphorous-containing acids may also be used.

In FIG. 1, the crosslinking substance applied to the mat 14 is obtained from a supply 19 thereof such as a tank or analogous vessel. It is also possible for the supply 19 of crosslinking substance to be continuously produced on-line to prevent pre-cure of the crosslinking substance that may occur over time if it were stored in a large vessel. On-line production of the crosslinking substance is particularly advantageous when it contains a catalyst. Alternatively, for example, a batch of the crosslinking substance can be prepared fresh each day, so long as no significant deterioration of the solution will occur during the period in which the batch is consumed.

Crosslinked cellulose fibers are individual fibers each comprising multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents". Suitable crosslinking agents are generally of the bifunctional type which create covalently bonded "bridges" between said neighboring hydroxyl groups.

Crosslinked cellulose fibers have particular applicability not only in wrinkle-resistant fabrics but also in materials derived from wood pulp having one or more desirable characteristics such as high loft, low density, high water absorbency, resiliency, and light weight. As a result, crosslinked cellulose fibers are candidates for use in absorbent structures found in disposable products such as diapers and pads. They are also useful for paper towelling, wiping cloths, filters, and other similar uses.

Despite their desirable qualities, crosslinked cellulose fibers have previously enjoyed limited success as a raw material. A principal reason for this is because the most convenient way for a manufacturer to crosslink cellulose fibers is by application of the crosslinking agent to a cellulosic fibrous sheet or mat which must be subsequently fiberized (all the constituent fibers of the sheet or mat separated from one another) before the fibers can be subjected to a step in which the crosslinking agent is cured. If any curing occurs before the fibers are completely separated, interfiber bonding can occur which would make any subsequent attempt at complete fiberization virtually impossible.

Crosslinked cellulose fibers when used in many products cannot have excessive amounts of certain defects known in the art as "knots" or "nits". Knots are agglomerations of fibers remaining after an incomplete fiberization of a cellulosic fibrous sheet. Nits may be defined as hard, dense agglomerations of fibers held together by the crossing substance due to the ability of crosslinking agents to covalently bond individual fibers together (interfiber bonding). Nits are generally regarded in the art as having a surface area of about 0.04 $mm^2$ to about 2.00 $mm^2$. A nit usually has a density greater than 0.8 $g/cm^3$, where a density of about 1.1 $g/cm^3$ is typical. The fibers comprising a nit virtually cannot be separated from one another in a conventional fiberizing device. As a result, these recalcitrant particles become incorporated into the final product where they can cause substantial degradation of product aesthetic or functional quality. For example, nits can substantially reduce the absorbency, resiliency, and lot of an absorbent product. For aesthetically sensitive products, such as high quality paper, a "nit level" of three or less (two or fewer nits per 6-inch diameter test "handsheet"; see Example 1) is generally regarded as a maximally acceptable number of nits. Knots can also seriously degrade product appearance. Also, as an example of the effect of these particles on product performance, filters made using crosslinked fibers containing any nits and knots would in many cases be incapable of performing to specifications.

Conveying Device

Referring further to FIG. 1, each mat 14 of cellulosic fibers is conveyed by a conveying device 12, which can comprise, for example, a conveyor belt or a series of driven rollers with the mat positioned therebetween. The conveying device 12 carries the mats through the fiber treatment zone 16. FIG. 1 also shows a further portion of one type of conveying device comprised of a first pair of rollers 26 and a second pair of rollers 28 for each mat 14. The first and second pair of rollers 26, 28 are particularly effective for urging the corresponding mat at a substantially constant and controlled rate of speed.

Fiberizer

The subsystem following the fiber treatment zone is a fiberizer 20 which serves to comminute one or more mats 30 impregnated with the crosslinking substance into individual substantially unbroken cellulose fibers comprising a fiber output. The fiberizer 20 performs its task on one or more mats, which are preferably still moist (but which may be dry) from application of the crosslinking agent. In this case, the wet sheets are delivered directly and immediately to the fiberizer by the conveyor 12 without aging or other significant delays. As detailed below, the preferred embodiment of the fiberizer 20 is designed to minimize interfiber bonding and the formation of nits therein. Also, the preferred embodiment of the fiberizer 20 thoroughly fiberizes each impregnated mat 30, thereby virtually eliminating residual knots.

The preferred embodiment of the fiberizer 20 comprises an attrition device 32 as detailed hereinbelow and in copending U.S. patent application Ser. No. 07/607,312 entitled "Fiberzing Apparatus", filed on Oct. 31, 1990, which is incorporated herein by reference. The attrition device 32 preferably can simultaneously fiberize a plurality of impregnated mats 30 and has a separate mat inlet 34a, 34b for receiving each corresponding impregnated mat.

Figure 2:
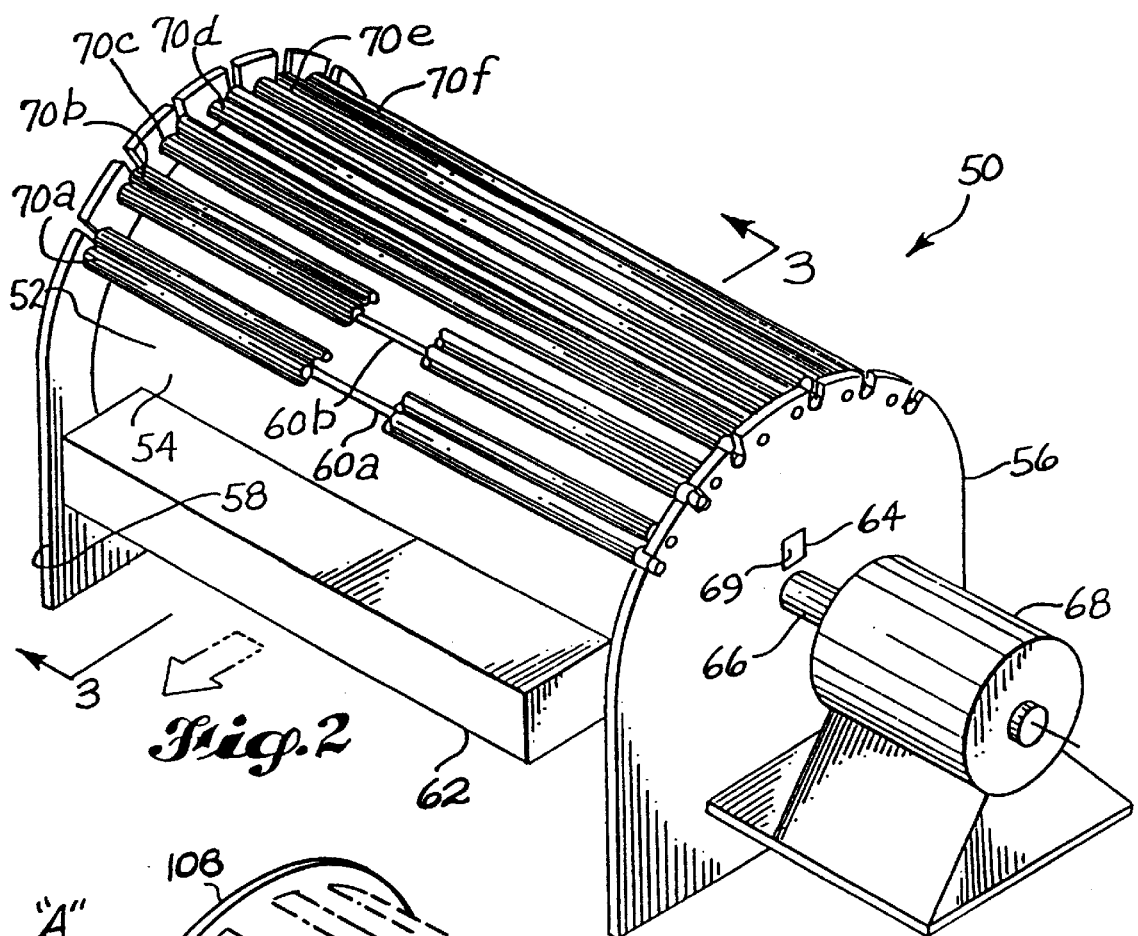
FIG. 2 is an isometric external view of a preferred embodiment of an attrition device, where certain details of the mat feeder assemblies have been omitted for clarity.

The exterior of a preferred embodiment of the attrition device 50 is shown in FIG. 2, which comprises an elongated cylinder-shaped housing 52 having an exterior surface 54. A first end panel 56 is located on one end of the housing 52 and a second end panel 58 is located at the other end of the housing 52. Multiple mat inlets (two of which 60a, 60b are shown) defined by the housing are located radially in an arc comprising a portion of the circumference of the housing 52, where each mat inlet is dedicated to feeding a separate mat into the attrition device 50. An outlet chute 62 extends from the housing 52. Each end panel 56, 58 defines a central orifice 64 through which coaxially extends a corresponding rotor shaft end 66 rotatable relative to the housing 52. One rotor shaft end 66 is coupled to a drive motor 68 serving to impart rotational motion thereto.

An air flow port 69 is provided through each end panel 56, 58. As a downstream blower 160 (discussed below) coupled to outlet 62 is operated, air is drawn in through openings 69, and around the ends of the rotor 100 (discussed below in connection with FIG. 4) to assist in minimizing the accumulations of fiber at such locations. Although variable, air typically flows at a rate of about 50 m$^3$/min through each of the openings 69. Also, a conduit (not shown) is typically included and coupled to wall 52 delivering water or other cleaning fluid to the interior of the housing through plural nozzle openings to clean any fiber accumulations from the attrition device. A liquid cleaning operation is typically accomplished by directing water toward the rotors in a direction somewhat counter to the direction of the normal rotor rotation as the rotor is rotated in this direction. Cleaning may be periodically performed, such as once every sixteen hours of operation of the attrition device, depending in part upon the volume of fiber being processed. By cleaning fiber accumulations in this manner, the accumulations do not end up in the finished product where they may comprise bonded nits.

Each mat inlet includes a feeder assembly, such as assemblies 70a–70f shown partially in FIG. 2, each mounted exteriorly relative to the cylindrical housing 52 at a location adjacent the corresponding mat inlet. A representative feeder assembly (such as 70d in FIG. 2) is shown in more detail in the transverse sectional view of FIG. 3. Each feeder assembly 70 is comprised of a first feed or seal roller 72 and a second feed or seal roller 74 extending longitudinally between the first and second end panels 56, 68 (FIG. 2). Also extending longitudinally between the first and second end panels 56, 58 are corresponding support angles or brackets (such as 76a and 76b in FIG. 3) and wedge-shaped alignment or mounting bars (such as 78a and 78b in FIG. 3). Since FIG. 3 only depicts one feeder assembly 70d, angles 76a and 76b correspond to the feeder assembly 70d. The first and second seal rollers 72, 74 extend longitudinally in a direction substantially parallel to, and have a length substantially equal to, the corresponding mat inlet 60a situated between a leg 80 of the angle bracket 76a and a leg 82 of the angle bracket 76b. The seal rollers 72, 74 are rotatably mounted for rotation about their respective longitudinal axes 84, 86 at locations equidistant from the mat inlet 60a. The distance D, from a plane through the axes of seal rollers 72, 74 to the effective rotor surface 144 swept by the hammers of the rotor 100 (FIG. 4) is preferably from about one-half inch to no more than about four inches when wet sheets are being fed to the rotor 100. This minimizes the possibility of plugging of the opening 60a as the sheets are being delivered thereto.

In one specifically preferred design, each seal roller has a central shaft and an outer roll. The ends of the central shaft of each seal roller 74 are coupled by a respective bearing to the end plates 56, 58. In addition, the ends of the central shaft of the seal rollers 72 are supported for rotation by a bracket (one being shown as 87 in FIG. 3). Typically the seal rollers are of a rigid material, such as steel, with the seal roller 74 being mounted at a fixed location. The ends of the shaft of the seal roller 72 are positioned within respective recesses 85 in the respective brackets 87. The bracket 87 may be pivotally coupled to the housing for pivoting in the direction of arrow 91 upon removal of a bolt or other stop 89. When bracket 87 is shifted upwardly in FIG. 3, the seal roller 72 may be removed for repair and or cleaning and to provide access to seal roller 74. Pneumatic cylinders, not shown, typically apply a load of from 5 psi to 80 psi to the respective ends of the shaft of the seal roller 72 to bias the seal rollers together. This pressure is typically relieved to allow the feeding of a sheet between the seal rollers and is then reinstated during normal operation of the attrition device. At least one of the seal rollers, such as roller 74, is rotatably driven via a motor (not shown) at a controlled angular velocity to advance a mat (not shown) situated between the first and second rollers 72, 74. Roller 74 may, for example, be driven in the direction of arrow 93 at a predetermined mat feed rate through the mat inlet 60a.

Figure 3:
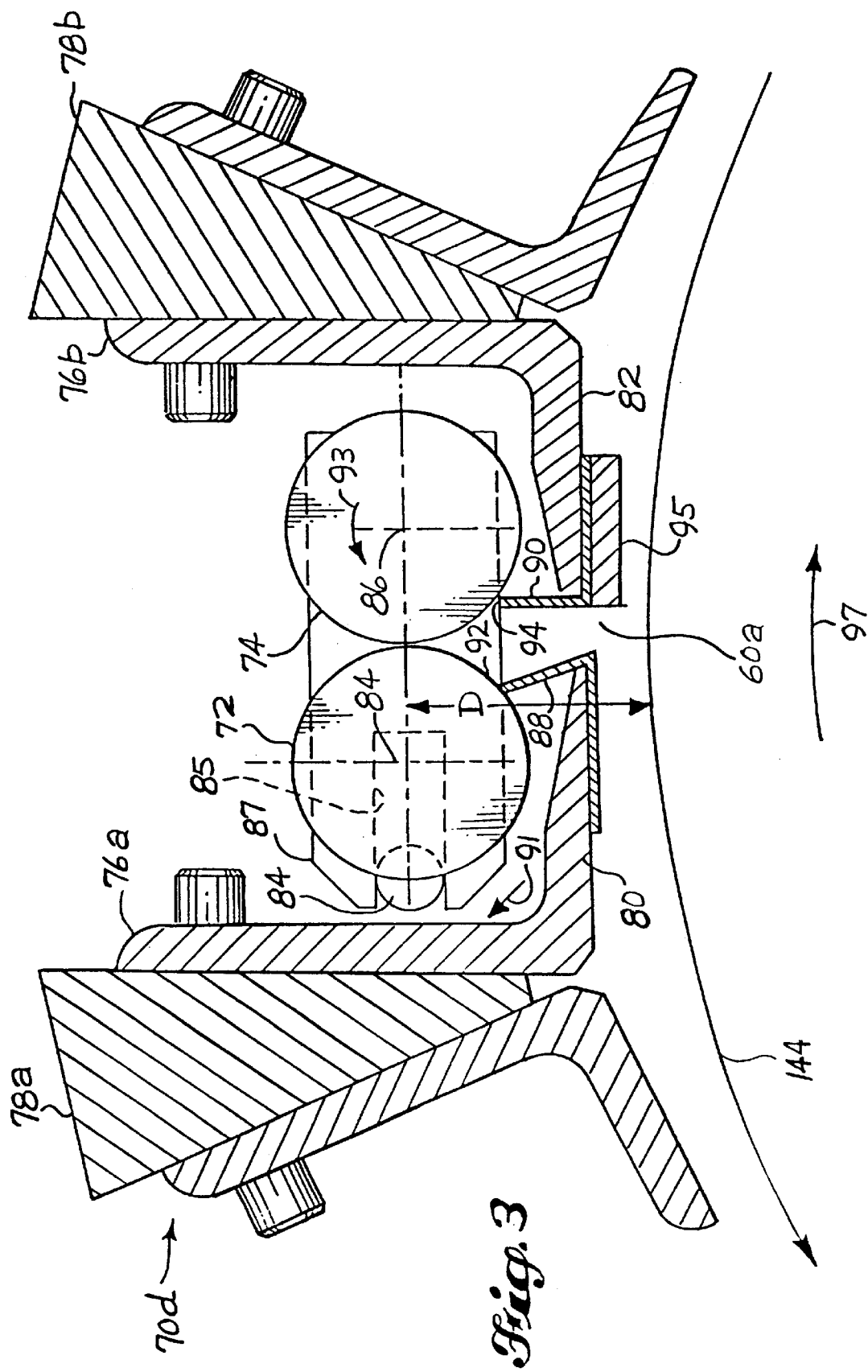
FIG. 3 is a transverse sectional view of a mat feeder assembly of the preferred embodiment of the attrition device.

A first guide 88 and a second guide 90 are also mounted to the corresponding mounting brackets 76a and 76b, respectively. Each of the guides 88, 90 extend longitudinally in a direction substantially parallel to the corresponding seal rollers 72, 74, respectively. Each guide 88, 90 is typically constructed of a rigid material and includes an outer edge 92, 94, respectively, adjacent to, but spaced from the surface of the corresponding seal roller 72, 74, respectively, along the full length of the roller. The guides 88, 90 thereby serve to substantially prevent air from passing past the guides and to the corresponding mat inlet 60a. Therefore, substantially all of the air drawn into the attrition device passes through the openings 69 (as previously explained). The fiber mat passing through inlet 60a passes an optional nose bar 95 and is delivered against the rotor 100 traversing the effective rotor surface 144 (FIG. 3). The gap between the inlet 60a and the effective rotor surface is typically no more than about one-fourth to one inch.

Figure 4:
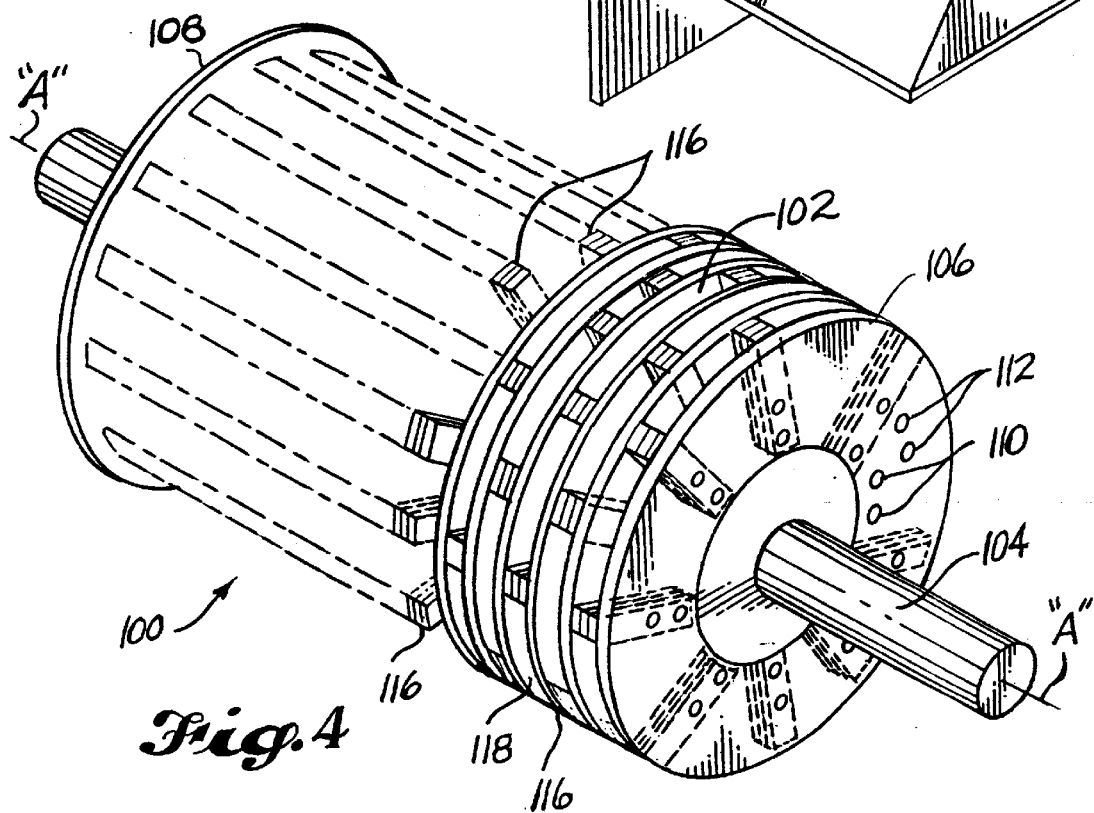
FIG. 4 is an isometric view of the rotor of the attrition device of FIG. 2.

FIG. 4 shows a rotor 100 of the type coaxially mounted inside the attrition device housing 52 (FIG. 1). The rotor 100 comprises a plurality of substantially annular spacer or hammer mounting plates 102 mounted to the rotor shaft 104. The plates 102 extend radially outwardly from the longitudinal axis "A" of the rotor shaft 104 and are parallel to one another. The rotor 100 also has a first rotor end plate 106 and a second rotor end plate 108, each substantially annular in shape and oriented parallel to the mounting plates 102. The first and second rotor end plates 106, 108 are mounted coaxially to the rotor shaft 104 and have a diameter sufficiently large such that only a narrow gap (e.g. one-sixteenth to one-half inch) is left between the inner surface of the cylindrical housing (not shown in FIG. 4) and the perimeter of the first and second end plates 106, 108. The illustrated plates 106, 108 extend radially outwardly beyond the distal ends of hammers 116 to minimize the possible accumulation of fibers adjacent to the end plates.

Attached to and extending between the first and second end plates are plural inner mounting rods 110 and an identical number of outer mounting rods 112 oriented parallel to the longitudinal axis "A" of the rotor shaft 104. The inner and outer mounting rods 110, 112 are secured to the first and second rotor end plates 106, 108. As shown clearly in FIG. 4, the mounting rods 110, 112 are arranged as plural equiangularly spaced pairs. Each pair comprises a single inner mounting rod 110 and a radially outwardly positioned single outer mounting rod 112. A typical rotor 100 has sixteen such pairs of rods arranged radially about the rotor axis "A".

Each pair of mounting rods 110, 112 has mounted thereto plural groups of hammer plates, each group comprising a hammer assembly 116. Each such hammer assembly 116 is located either between adjacent mounting plates 102 or between a spacing plate 102 and an adjacent rotor end plate 106, 108. However, each hammer assembly 116 is spaced from an adjacent hammer assembly 116, by an empty space 118 large enough to accommodate another hammer assembly. As a result, on a rotor 100 with twenty-seven mounting plates 102 and two rotor end plates 106, 108, for example, the maximal number of hammer assemblies 116 held by a given pair of mounting rods 110, 112 is fourteen.

A representative flat hammer plate 130 of assembly 116 is depicted in FIG. 5, wherein each hammer plate 130 has a proximal end 132 positioned toward the rotor axis (not shown) and a distal end 134 positioned radially outward relative to the rotor axis. The hammer plate 130 also defines two mounting holes 136a, 136b for attaching the hammer 130 to an associated pair of mounting rods 110, 112 (not shown in FIG. 5). The distal end surface 134 of the hammer plate has a trailing edge 138 and a leading edge 140, wherein the leading edge 140 extends radially outward relative to the rotor axis beyond the trailing edge 138. The distal end 134 is cut at a five degree angle relative to a line 142 parallel to the proximal edge 132. The direction of rotation of the rotor is indicated by an arrow 145 in FIG. 5.

As shown in FIG. 6, each illustrated hammer assembly 116 comprises plural planar plate-like hammers 130 (three being shown in this figure). These plates are typically spaced apart by spacers (not shown). Each of said hammer assemblies 116 located between adjacent mounting plates 102 (only one plate 102 being shown in this figure) also includes a left-angled hammer 146 and a right-angled hammer 148 each having a lip 150a, 150b, respectively, extending transversely in an opposing direction relative to each other. The width dimension 152 of the lip of each angled hammer is typically equal to or slightly less than half the thickness dimension of a mounting plate 102. Also, each of the hammer assemblies 116 located between a plate 102 and a rotor end plate replaces one of the L-shaped hammers with a flat hammer plate adjacent to the end plate. Other hammer configurations and arrangements may be used. However, a preferred hammer arrangement minimizes any gaps in the surface swept by hammer elements to preferably no more than one-fourth of an inch.

The illustrated embodiment 50 of the attrition device is operated by driving the rotor 100 at a high angular velocity while feeding one or more impregnated mats through one or more corresponding mat inputs. The mat is urged at a controlled linear velocity into the corresponding mat input slot 60 by the controlled rotation of the feed rollers 72, 74. As the impregnated mat enters a mat inlet, it is repeatedly impacted by the distal end surface and in particular, the leading edge of the hammer plates, which effectively and completely comminutes the mat into its individual constituent fibers, substantially free of knots and nits.

The preferred embodiment 50 of the attrition device as described hereinabove is particularly effective in simultaneously fiberizing one or more separate mats (up to six) to form a volume of individualized cellulose fibers having a nit level substantially lower than levels achievable with existing attrition devices such as hammermills. This is believed to be due to the fact that the present attrition device lacks hot spots and dead spaces, wherein fibers can accumulate, found in conventional hammermills or other attrition devices currently used in the art.

Referring further to FIG. 1, a first conveyor fan 160 of conventional design can be utilized for propelling the fibers from the outlet 62 of the attrition device 32 through a conduit 162.

An optional component of the fiberizer 20 is a first cyclone 164 or similar apparatus known in the art utilized in a conventional manner to concentrate the fibers passing out of the outlet 62 of the attrition device 32. The first cyclone 164 receives the fibers through the conduit 162 coupled thereto.

Excess air can be recovered at the top 166 of the first cyclone 164 and recycled as required through a conduit to a location upstream of the first conveyor fan 160 (if used). Such additional air can be beneficial for easing the transfer of the fibers through the first conveyor fan 160.

A disk refiner 168 is another optional component of the fiberizer 20 which can be employed to effect additional separation of fibers (removal of knots) if required. The disk refiner 168 is of a type known in the art and comprises a disk refiner inlet 170 and a disk refiner outlet 172. A representative disk refiner 168 is type DM36 manufactured by Sprout-Bauer, Incorporated of Muncie, Pa. If the disk refiner 168 is used, the inlet 170 thereof is coupled via a conduit 174 to an outlet 176 of the first cyclone 164.

A second conveyor fan 178 may optionally be utilized to urge propagation of the fibers through a conduit 180 downstream of the disk refiner 168. Excess air can be recovered from the top 166 of the first cyclone 164 and routed via a conduit 181 to a tee 182 just upstream of the second conveyor fan 178.

Another optional component of the fiberizer 20 is a fluff generator 190 which receives the fibers from the optional second conveyor fan 178 through a conduit 184. The fluff generator is described in detail below and in copending U.S. patent application Ser. No. 07/607,157 entitled "Multi Pin Rotor Fiber Fluff Generator", filed on Oct. 31, 1990, incorporated herein by reference.

Referring now to FIG. 7, a preferred embodiment of the fluff generator 190 comprises a housing 192 shaped in the form of three contiguous, partially intersecting cylinders, including a first housing portion 194 opening into a second (or middle) housing portion 196, which opens into a third housing portion 198. Each housing portion 194, 196, 198 has a longitudinal coplanar axis A1, A2, A3, respectively. The housing 192 has an inlet 200 permitting delivery (arrow 202) of fibers to the first housing portion 194, and an outlet 204 conducting fluffed fibers away (arrow 206) from the third housing portion 198.

As shown in FIG. 8, showing a transverse sectional view of the first housing portion 194, the interior surfaces 212 of each of the first, second, and third housing portions have affixed thereto multiple stator pins 214 radially pointing toward the respective axis of the housing portion. The pins 214 are grouped in longitudinally extended rows along lines parallel to the respective housing portion axis.

Each of the first, second, and third housing portions 194, 196, 198, respectively, is in surrounding relationship to a first rotor 216, a second rotor 218, and a third rotor 220, respectively, as shown in FIG. 9. Each rotor 216, 218, 220 has a corresponding rotor shaft 222, 224, 226, coaxial with the axis A1, A2, A3 of the respective housing portion. As shown in FIG. 8 (showing a transverse sectional view of the first housing portion 194 only, but applicable to illustrate similar details inside the second housing portion 196 and third housing portion 198) and FIG. 9, to the shaft 222 of the rotor 216 are mounted four longitudinally extended rows of plural rotor pins 228, where each row of rotor pins 228 is equiangularly spaced in a radial manner around the corresponding rotor shaft 222. The rotor pins 228 radially extend from the shaft 222 nearly to the inside surface 212 of the corresponding housing portion 194 but are positioned on the rotor shaft 222 such that they will pass between longitudinally adjacent stator pins 214 when the rotor 216 is rotating about its axis. Rotor shafts 224 and 226 are similarly equipped with rotor pins 228.

As shown in FIG. 9, each rotor shaft 222, 224, 226 has a first end 230, 232, 234, respectively, and a second end, 236, 238, 240, respectively, each extending through and journaled in the corresponding housing portion 194, 196, 198, respectively. The first and second ends of each rotor shaft extend outside the corresponding housing portion. A pulley 242a, 242b is attached to each of the first ends 230, 232, respectively, of the first and second rotor shafts 222, 224, respectively. Likewise, a pulley 244a, 244b is attached to the second ends 238, 240, respectively, of the second and third rotor shafts 224, 226, respectively. The first end 234 of the third rotor shaft is rotatably coupled directly or indirectly to a drive motor 250. Each set of pulleys is coupled by a drive belt 252a, 252b ensuring that, when the drive motor 250 rotates the third rotor 220, the second and first rotors 218, 216, respectively, synchronously rotate in the same rotational direction as the third rotor 220.

The fluff generator 190 is operated by synchronously driving the rotors 216, 218, 220 at a high rotational speed and conducting fibers 202 (FIG. 7) from their disk refiner 168 (FIG. 1), where the velocity of said fibers is increased via the second conveyor fan 178, into the inlet 200 of the fluff generator 190. The fibers are conducted sequentially through the first, second, and third housing portions 194, 196, 198, respectively, and exit 206 the fluff generator 190 through the outlet 204. As the fibers pass through the housing 192 of the fluff generator 190, they encounter strong agitation and turbulence generated by the groups of rotor pins 228 on each of the three rapidly rotating rotors 216, 218, 220 passing by the stationary stator pins 214. By encountering such turbulence and agitation, any knots remaining in the fibers are comminuted to form a fiber output containing virtually no knots.

As used herein, the "fiber output" is the mass of thoroughly individualized fibers exiting the fiberizer 20 and passing to the dryer 22.

As discussed hereinabove, the disk refiner 168 and fluff generator 190 are optional components of the present apparatus 10. In most cases, the attrition device 32 alone is adequate for completely fiberizing plural mats. However, in cases where the mats are unusually bulky, the disk refiner 168 and fluff generator 190 can be employed, particularly to ensure the absence of knots in the fiber output.

Dryer

Referring further to FIG. 1, a preferred embodiment of the present apparatus 10 includes a dryer 22 which is utilized to perform two sequential functions: remove residual moisture from the fibers and cure the crosslinking agent. Preferably, the dryer 22 comprises a drying introduction zone 273 for receiving fibers e.g. from fluff generator outlet 204 and for removing residual moisture from the fibers via a "flash drying" method and another drying zone 260, 262 for curing the crosslinking agent. In FIG. 1, the curing starts in zone 260 and continues through zone 262.

The FIG. 1 embodiment shows that zone 273 is coupled to the fluff generator outlet by a conduit 272 and to a source 274 of heated air, typically produced by combustion of a supply of natural gas 276 and fresh air 278. The temperature of heated air is regulated to maintain the temperature of the drying zone 273 within a range of about 200° C. to about 315° C. To achieve this temperature in zone 273, air is blown from source 274 at a temperature, for example, of about 260° C. The drying zone 273 is a J-shaped conduit that includes a necked down or reduced diameter conduit having an initial portion 273a, and a right angle portion 273b that flares to increase the diameter of the conduit as it connects with the inlet 268 of the expansion chamber defined by body 266 of drying zone 260. The diameter of the reduced diameter portion conduit is reduced compared to the diameter of the conduit 272 through which the fibers flow from the fiberizer. The diameter reduction increases the velocity of the flow of fibers and causes a decrease in pressure that promotes rapid evaporation and drying of the fibers in portion 273a. The fiber output in conduit 272 is introduced into the reduced diameter portion 273b of conduit 273 at inlet 275 immediately downstream from where portion 273a necks begins.

As the fiber output passes into the drying zone 273 at inlet 275, the wet fibers comprising the fiber output are substantially instantaneously exposed to the high temperature in this zone. Such rapid exposure to high temperature imparts a "flash drying" effect to the fibers, thereby causing rapid and thorough drying. Such "flash drying" also tends to separate, in a microscopically explosive manner, fibers that are touching one another, thereby ensuring thorough separation of the fibers. The passage time through the drying zone 273 is preferably less than one second, which is deliberately kept short to avoid overheating and scorching the fibers, which become highly susceptible to scorching after the residual moisture has been driven therefrom.

As the fibers enter the expanding throat of section 273b and enter first drying zone 260, pressure changes enhance the microscopic fiber explosions as water vapor is rapidly released from the fibers and pushes the fibers apart. This expanding throat 273b mates with an expanding inlet 268 to an expansion chamber defined by first drying zone 260. The FIG. 1 embodiment shows that the first drying zone 260 comprises a first tower 264 having a body portion 266, an inlet 268, and a first tower outlet 270. The dryer zone 273 is coupled via conduit 272 to the outlet of the fluff generator 190. Since the fluff generator 190 is an optional component, it is also possible to couple the dryer introduction zone 273 directly to the outlet 62 of the attrition device 32 if neither the fluff generator 190 nor the disk refiner 168 are included.

In FIG. 1, the first tower outlet 270 is shown preferably coupled via a conduit 280 to a down tube 282, which is coupled via a conduit 284 to a third conveyor fan 286 located at an inlet 288 of a second tower 290. The third conveyor fan 286 performs the function of transporting the fibers through the dryer which thereby pass through the inlet 288 of the second tower 290.

The second tower 290 is shown which includes the inlet 288, a second tower body 292, and an outlet 294 serving as an outlet of the dryer 22. Dried fibers are propelled through the inlet 288 of the second tower 290 via the third conveyor fan 286. As the fibers are lofted through the second tower body 292, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as not to scorch the fibers during curing. It should be noted that single stage dryers may also be used.

The dried and cured fibers exiting the dryer outlet 294 have an extremely low level of nits and virtually no knots. Further, they are not discolored from scorching and the like, and have a median fiber length substantially unchanged from the median length of the fibers comprising the mat 14.

FIG. 1 also shows a second cyclone 300 of conventional design coupled via a conduit 302 to the dryer outlet 294, serving to concentrate the fibers passing therethrough in preparation for collection. Excess air 304 is vented through the top 306 of the second cyclone 300. The resulting concentrated fibers can be collected using any of a number of collection devices 308 known in the art, such as fiber bagging devices.

It is possible to add retention bins to the system of FIG. 1 to increase curing time of the crosslinking agent. Such a bin 310 is shown between cyclone 300 and collection device 308. Bin 310 has the shape of an inverted pyramid, and is large enough to hold the output from cyclone 300 for a period of 1–5 minutes when the system is operating. The bin is preferably heated to a temperature of about 175–190° C. to promote curing of the crosslinker. The most preferred temperature within this range may vary with the capacity of the bin, because larger retaining bins will allow longer residence times at lower temperatures. A bin with a sufficient capacity to collect 5 minutes of output from cyclone 300 could, for example, be heated to a temperature of 175° C. A smaller bin with only a three minute capacity, however, may require a residence temperature of 180° C. Very small retention bins, for example bins with a one minute capacity, may have a bin temperature of 190° C. to promote curing of the crosslinking agent in the shorter period of time.

Figure 11:
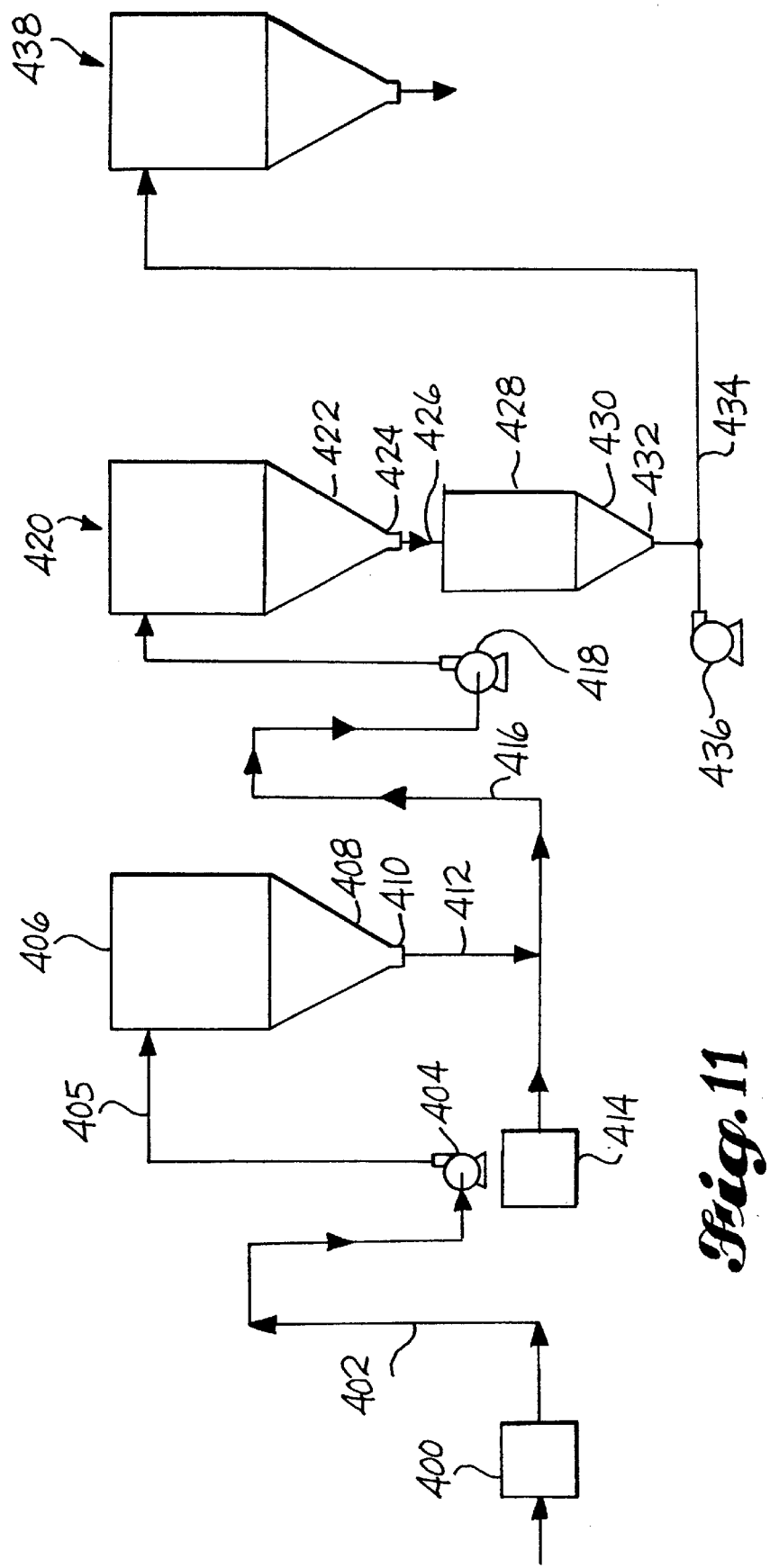
FIG. 11 is an alternative view of the system showing a retention bin that allows curing of the crosslinking agent after the fiber is dried.

An alternative crosslinking system having a retention bin is shown in FIG. 11, in which an air heater 400 propels fibers through a conduit 402. The fibers which enter conduit 402 have already been saturated with the crosslinking agent, and the fibers begin to dry as they are moved through heated conduit 402 by a conveyor fan 404 into a conduit 405. Fibers are then introduced tangentially from conduit 405 into a top cylindrical area of a first dryer 406, and then fall downwardly. The bottom portion of dryer 406 tapers at 408 to an outlet 410 such that partially dried fibers are withdrawn through a conduit 412 and propelled by a second heated air blower 414 through a conduit 416. Movement of partially dried fibers through conduit 416 is assisted by a second conveyor fan 418, which helps propel the partially dried fibers tangentially into a top cylindrical zone of a second dryer 420. Dryer 420 tapers at 422 to a restricted outlet 424 through which fibers are withdrawn through a conduit 426 and emptied into a retention bin 428. Bin 428 has a tapering bottom portion 430 with a selectively closed outlet 432 through which cured fibers may be withdrawn from the retention bin at preselected intervals when the bin is filled to capacity. When outlet 432 is opened, fibers are introduced into a conduit 434, whence they are conveyed by a conveyor fan 436. Heated air is not introduced into conduit 434, hence cooling of the fibers occurs as they travel through conduit 434 and are collected in a collection bin 438.

EXAMPLE I

In one specific embodiment of the invention, the fibers are moved through conduits 402, 405 at a temperature of about 250° C. First dryer 406 is approximately 50 feet tall, and has a largest diameter of 14 feet in its cylindrical upper portion. The heated fibers undergo a flash evaporation as they enter the relatively low pressure environment of large diameter tank 406. The partially dried fibers then exit through conduit 412 at a temperature of about 60° C., and are once again heated to about 250° C. by hot air from air heater 414 blowing through conduit 416. Flash evaporation of the fibers once again occurs in dryer 420, which in this example is approximately 60 feet tall and has a largest diameter of about 16 feet in its cylindrical upper portion. The flash dried fibers exit dryer 420 through outlet 424 and are collected in retention bin 428. The bin has a sufficient capacity to collect fiber output from dryer 420 for a period of 60 seconds. The retention bin is maintained at a sufficient temperature, for example 190° C., to allow the crosslinking agent to cure during the 60-second period of retention in bin 438. At the end of a 60-second retention period, the fibers are withdrawn through outlet 432 and conveyed through conduit 434 to holding tank 436.

EXAMPLE II

In this example, non-woven fibrous mats were impregnated with a crosslinking agent, fiberized, dried, and cured using the apparatus as diagrammed schematically in FIG. 1.

Two 52-inch wide mats of southern pine kraft wood pulp fibers (type NB316 from Weyerhaeuser Company) and having a basis weight of 680 g/m$^2$ were fed to the apparatus. The mats were impregnated using dimethyloldihydroxy-ethylene urea at a concentration of about 5%, applied over both sides of each mat using a combination of spray nozzles and impregnation rollers. The loading level of crosslinking agent was about 4.5% w/w.

The treated fiber mats were fed at the rate of 8 meters/minute to the attrition device 32. The specific attrition device used in this example was equipped with six mat inlets and a rotor having 16 rows of hammers as described above around the circumference of the rotor. The rotor had a diameter of 30 inches and was rotated at an angular velocity of 1200 rpm by an electric motor. Other rpm rates have also been tested and have proven satisfactory, including extremely high rpm rates.

Random samples of fibers were obtained from the output attrition device and observed for nits. These samples were 2.6 grams and were consistently observed to have fewer than three nits on the average with most samples having no nits. The attrition device was flushed with water once every sixteen hours for cleaning purposes.

A disk refiner was employed downstream of the attrition device. This specific disk refiner was a DM36 refiner as previously mentioned.

A fluff generator as described in FIGS. 7–9 was also employed in this downstream of the disk refiner.

The temperature at the dryer input 273 in this example was within the range of 200° C. to 315° C., and conduit 273*a* had a diameter of 3½ feet. The tower body 266 that formed zone 260 had a diameter of 7 feet, hence the diameter ratio of conduit 273*a* to tower 266 was 1:2. The temperature at the second tower outlet 294 was within the range of 140° C. to 180° C.

Crosslinked fiber at the output of the dryer was produced at a rate of about 5000 pounds per hour and had a nit level on an average of from 1 to 3 and a maximum bulk of greater than 22. Bulk and nit levels were determined by the following procedure, involving the production of test "handsheets" with a diameter of about 6 inches:

A "British handsheet mold" was filled with 3 to 4 inches of water. To approximately 750 mL of water were added 1.2 grams of pulp, available from Weyerhaeuser Company, followed by agitation using a Waring blender for 20 seconds to yield a pulp slurry. A 2.4 gram sample of the above obtained crosslinked fiber was added to the pulp slurry in the blender followed by agitation therein for another 10 seconds. The resulting slurry was added to the handsheet mold up to a fill mark. The slurry in the mold was gently mixed using a spatula for 3 seconds, then drained, leaving the pulp wet laid on the screen in the mold. The wet pulp layer was blotted to remove as much moisture as possible, then removed from the screen. The resulting handsheet was dried between two blotters on a drum dryer, then weighed to the nearest 0.01 gram immediately after drying.

Bulk was determined using a caliper, performed immediately after drying. Mean thickness was determined using five thickness determinations of various locations on the handsheet. Bulk was calculated in units of cm$^3$/g as follows:

$$\frac{\text{(mean thickness) cm (20.38) cm}^2}{\text{(Handsheet weight) grams}} = \text{Bulk}$$

Nit level was determined by examination of the handsheet and simple determination of the number of nits present on the handsheet. If no nits were observed a nit level of 1 was assigned to the test sheet; if 1 nit was observed, a nit level of 2 was assigned to the sheet; if 2 nits were observed, a nit level of 3 was assigned to the sheet; and so forth for higher nit levels.

Therefore, the apparatus of the present invention effectively produces a low nit level product, and one of high bulk even when crosslinking agents are used.

Fiber Thermobonding

One problem with the fiber crosslinking method of the present invention is that it may produce a wet laid sheet having reduced tensile strength. The intrafiber crosslinking in the cellulose chemically inhibits interfiber bonds that give integrity to a web. As a result, it is sometimes difficult to make a wet laid sheet with the dried and cured crosslinked fibrous output of the present invention. The present inventors have overcome this problem by adding a thermobonding agent to the dried and cured individual cellulose fibers to form a mixture that is made into a wet laid web. The web is then heated to a sufficient temperature to activate the thermobonding material and increase the wet strength of the web by providing a thermoplastic matrix within the web. Addition of a thermobonder can also be used to increase the tensile strength of an air laid web.

A number of synthetic fibers have been developed in recent years which are heat-adhesive (thermobondable) synthetic fibers. These thermobondable synthetic fibers can be used to bond fibers together, thereby providing an absorbent material with improved strength that allows thinner and lighter weight products to be produced. Examples of patents describing such fibers, or their use or production, are U.S. Pat. Nos. 4,189,338 (non-woven fabric comprising side-by-side bicomponent fibers); 4,234,655 (heat adhesive composite fibers); 4,269,888 (heat adhesive composite fibers); 4,425,126 (fibrous material using thermoplastic synthetic fibers); 4,458,052 (absorbent material containing polyolefin pulp treated with a wetting agent); 4,655,877 (absorbent web structure containing short hydrophilic thermoplastic fibers); and European Patent Application No. 248,598 (polyolefin-type nonwoven fabric). Thermobonding agents are commercially available, for example Celbond® dual-polymer (bicomponent) fibers from Hoechst Celanese Corporation of Somerville, N.J. Examples of other commercially available thermobonding agents include Vinyon® monocomponent fiber made by Hoechst Celanese from a copolymer of polyvinyl chloride and polyvinyl acetate, and Kodel® 100% polyester monocomponent fiber from the Eastman Kodak Company of Rochester, N.Y.

The manufacture and use of thermobondable bicomponent synthetic fibers is fully disclosed in European patent application publication number 340,763, filed Mar. 5, 1989, the disclosure of which is incorporated by reference. Briefly summarized, the bicomponent fiber comprises an inner core component and an outer sheath component in which the core component is a polyolefin or polyester, the sheath component is a polyolefin, and the core component has a higher melting point than the sheath component. The core is preferably surrounded by a coaxial sheath, in which the core component typically has a melting point of at least about 150° C., while the sheath component typically has a melting point of about 140° C. or lower. The sheath component is preferably selected from the group consisting of polyethylene, polypropylene, poly(1-butene), and copolymers and mixtures thereof, while the core component is selected from the group consisting of polypropylene, poly(1,4-cyclohexylene-dimethylene-terephtalate), poly(4-methyl-1-pentene), polyester and copolymers and mixtures of the foregoing. The weight ratio of the sheath and core components in the bicomponent fiber is preferably in the range of 10:90 to 90:10, more preferably from about 30:70 to 70:30, and most preferably from about 40:60 to 65:35. The cross-section of the fiber is preferably circular and has a fineness of about 1–7 decitex. The fiber is cut to a length of about 3–24 millimeters, typically about 5–20 millimeters, preferably about 6–18 millimeters.

The wet strength of a crosslinked cellulose material in accordance with the present invention can be increased with the thermobondable bicomponent fibers by subjecting the bicomponent fibers and crosslinked fibers to blending. The bicomponent fibers and non-bicomponent fibers can be blended, for example, by dispersion in water in a wet-laid nonwoven production process, so as to obtain a nonwoven web in which the bicomponent fibers are distributed in a substantially random and homogenous manner.

The percentage weight of bicomponent fibers in the fluff is preferably in the range of about 5–50%, more preferably 20–40%. The nonwoven web should contain a certain minimum amount of the bicomponent fibers in order that the improved characteristics due to the supporting structure of the thermobonded bicomponent fibers can be achieved. Thus, a bicomponent fiber content of about 5% is regarded as being the usual minimum. On the other hand, the bicomponent fibers of the present invention need not necessarily constitute a large portion of the fluff If a large amount of bicomponent fiber is added to the mixture, the physical properties of the bicomponent fiber will begin to predominate over the desired characteristics of the crosslinked fiber, such as high bulk and absorbency. One of the advantages of the bicomponent fibers of the present invention is that they can be used in low amounts. The weight ratio of the bicomponent fibers to the non-bicomponent fibers in the fluff can therefore be about 5:95–10:95.

Figure 12:
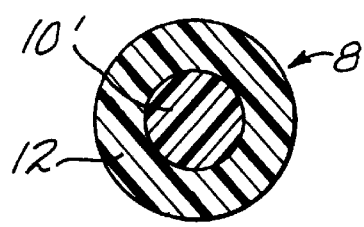
FIGS. 12 and 13 are cross-sectional views of concentric and acentric bicomponent fibers for incorporation into fibrous mats containing the individualized fibers produced by the method of the present invention.
Figure 13:
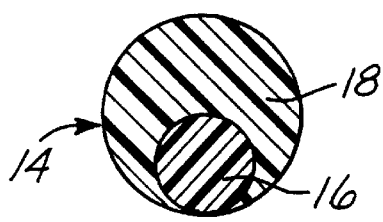

FIG. 12 shows a cross-section of a bicomponent fiber 8 with a concentric configuration. A core component 10 is surrounded by a sheath component 12 with substantially uniform thickness, resulting in a bicomponent fiber in which the core component 12 is substantially centrally located. FIG. 13 shows a cross-section of another bicomponent fiber 14 with an acentric configuration. A core component 16 in this configuration is substantially surrounded by a sheath component 18 with a varying thickness, resulting in a bicomponent fiber in which the core component 16 is not centrally located.

Figure 14:
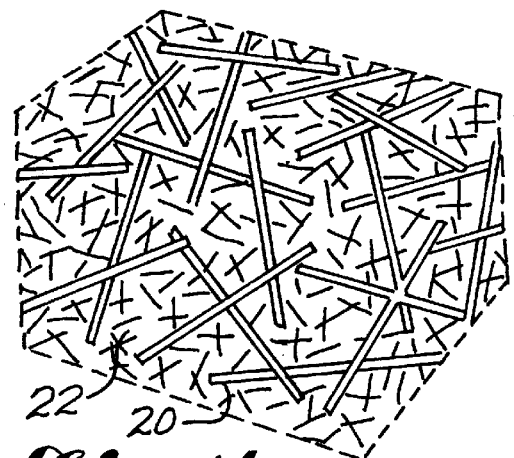
FIG. 14 shows the fibrous mat of the present invention containing long bicomponent fibers (prior to thermobonding).
Figure 15:
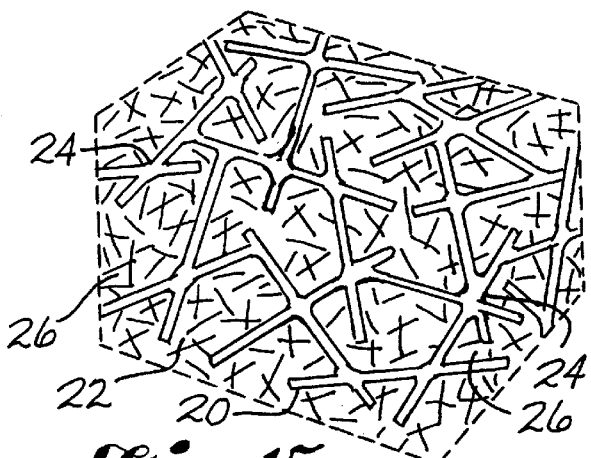
FIG. 15 shows a matrix structure formed by the bicomponent structures in the mat after thermobonding.

FIG. 14 shows the structure of a nonwoven web prior to thermobonding. Bicomponent fibers 20, according to the present invention, are arranged in a substantially random and homogenous manner among non-bicomponent fibers 22 in the fluff FIG. 15 shows the same structure as illustrated in FIG. 14, but after thermobonding. The sheath component of the bicomponent fibers has been melted by the thermobonding process, fusing the intact core components together (as at 24), thus forming a supporting three-dimensional matrix. The non-bicomponent fibers 22 are randomly arranged in the spaces defined between the bicomponent fibers, and some of the non-bicomponent fibers 22 have been fused (as at 26) to the bicomponent fibers.

Figure 16:
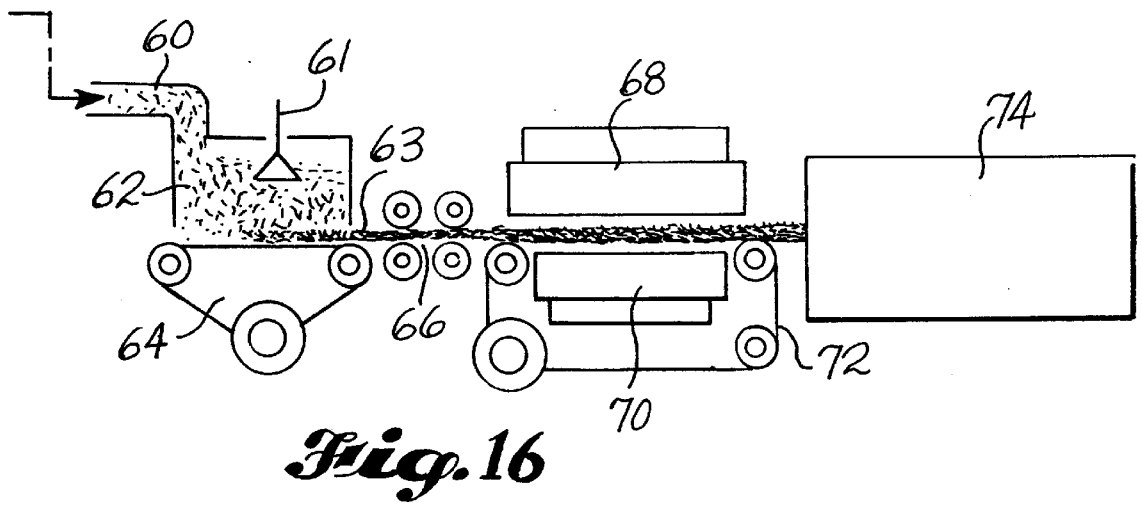
FIG. 16 is a schematic view of air laid equipment for producing the thermobonded absorbent material of the present invention.

FIG. 16 illustrates an air laid method by which the mixture of bicomponent and non-bicomponent fibers is fused to achieve the transition shown between FIG. 14 and FIG. 15. The mixture of cellulose fibers and thermobonding agents is introduced through an inlet 60 to a fluff mat forming hood 62, where a fluff mat 63 is formed by suction of the fibers onto a wire mesh 64. A layer of superabsorbent polymer (SAP) may be sprinkled on top of mat 63 to form a top SAP layer or introduced about halfway through formation of mat 63 to form a middle SAP layer. The fluff mat 63 typically passes through a series of rollers 66, in which the mat 63 is condensed or embossed prior to the thermobonding process. The mat 63 is then led via a second wire mesh 72 past a through air oven 68, which thermobonds the material, thus producing the supporting structure formed by the core component of the bicomponent fibers, as shown in FIG. 15. The thermobonded material is then led to a converting machine 74, in which the production of hygiene absorbent products, such as diapers, takes place.

The following examples will illustrate use of Celbond® K-56 bicomponent fiber with the intrafiber crosslinked fibers of the present invention.

EXAMPLE III

A slurry was prepared containing 20% weight percent of 0.4 inch long Celbond® K-56 type bicomponent fiber, and 80% of high bulk additive (HBA) fibers, prepared as in Example II. The bicomponent and BBA fibers were mixed in water at a consistency of approximately 0.01%. This slurry was dewatered on the forming wire of an inclined wire Fodrinier-type wet-laid nonwoven machine, and subsequently transferred, while still containing approximately 50% water, to a rotary through-dryer, which served to both fully dry the web and partially fuse the bicomponent Celbond® portion of the web. The basis weight of the dried web was 275 gsm, with a bulk density of approximately 0.03 g/cc. A control web, formed using conventional woodpulp at the 80% level in place of the HBA, resulted in a web with a bulk density of 0.1 g/cc. The resulting HBA/Celbond® dried and fused web possesses sufficient integrity to allow handling in further conversion steps, e.g., slitting/winding.

EXAMPLE IV

The bonded web of Example III is treated with a secondary binder treatment in order to develop specific properties in the web while maintaining its desirable low-density characteristics. A saturant is prepared by diluting a suitable binder product (such as Airflex 120 latex, manufactured by Air Products and Chemicals, Inc. of Allentown, Pa.) with water to a solids content of 5% from its original solids content of 52%. Airflex 120 is a self-crosslinking vinyl acetate-ethylene polymer, possessing low Tg (−20° C.) which results in the combination of tensile strength, abrasion resistance and flexibility in substrates to which it is applied. The bonded web of Example III is saturated in a bath of the diluted latex, then passed through a set of nip rollers which squeeze out excess latex, resulting in a web containing approximately 100% of saturant based on the weight of the dry web. The highly resilient nature of the HBA fibers in the web causes the web exiting the nip of the squeeze rollers to regain approximately the same thickness as that entering the nip, and thus allow retention of the low density nature of the web. This saturated product is then dried without compression in a suitable apparatus such as an oven at a temperature below 127° C., the melting point of the Celbond® sheath polymer. This heating step dries the web and crosslinks the Airflex 120 polymer without affecting the integrity of the web which might be reduced by re-melting the Celbond® sheath polymer. The low-compression drying is required to avoid crosslinking the binder while the web is in a densified configuration. The final product is a strong, flexible, resilient, abrasion-resistant web suitable for packaging delicate or abrasive articles.

EXAMPLE V

Lightweight (50–100 g) thermobonded HBA pads, either as-is or with subsequent binder treatment, are suitable for use as a "cushion layer" in a diaper or similar absorbent constructions, providing a means to rapidly wick moisture away from the top surface of the construct to a lower, relatively heavy, absorbent core. The thermobonded pad provides resistance to flow back to the upper surface because of relatively high thickness of the cushion layer.

Having illustrated and described the principles of the present invention in a preferred embodiment and variations thereof, it should be apparent to those skilled in the art that the invention can be modified in arrangement and detail without departing from such principles. We claim all modifications coming within the spirit and scope of the following claims.

What is claimed is:

1. A method for producing crosslinked cellulose fibers comprising the steps of:

applying a crosslinking substance to a mat of cellulose fibers at a fiber treatment zone;

conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;

separating the cellulose fibers in the fiberizer by hammering them into the fiber output of the substantially unbroken individual cellulose fibers without curing the crosslinking substance; and thereafter drying and then curing the crosslinking substance to crosslink the individual cellulose fibers, wherein the drying step comprises drying the fibers at a temperature of about 200–315° C. so as to flash evaporate water from the fiber output and form the dried fibers.

2. A method for producing crosslinked cellulose fibers, comprising the steps of:
applying a crosslinking substance to a mat of cellulose fibers at a fiber treatment zone;
conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;
separating the cellulose fibers in the fiberizer by hammering them into output of the substantially unbroken individual cellulose fibers without curing the crosslinking substance; and
thereafter drying and then curing the crosslinking substance to crosslink the individual cellulose fibers, wherein the fibers are cured at a temperature of about 140–180° C.

3. A method for manufacturing crosslinked cellulose fibers and converting the crosslinked fibers into a web, comprising the steps of:
applying a crosslinking substance to a mat of cellulose fibers at a fiber treatment zone;
conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about there;
separating the cellulose fibers in the fiberizer by hammering them into output of the substantially unbroken individual cellulose fibers without curing the crosslinking substance;
thereafter drying and then curing the crosslinking substance to crosslink the individual cellulose fibers, and adding a thermobonding agent to the dried and cured individual cellulose fibers, to form a mixture that is made into a web, then heating the web to a sufficient temperature to increase the wet strength of the web.

4. The method of claim 3 wherein the thermobonding agent is a bicomponent fiber comprising a core component and a sheath, wherein the core component has a higher melting point than the sheath component.

5. The method of claim 4 wherein the sheath component is selected from the group consisting of polyethylene, polypropylene, poly(1-butene), and copolymers and mixtures thereof, and the core component is selected from the group consisting of polypropylene, poly(1,4-cyclohexylene-dimethylene-terephtalate), poly(4-methyl-1-pentene), polyester and copolymers and mixtures of the foregoing.

6. The method of claim 4 wherein the core is polypropylene and the sheet is polyethylene, and the heating step comprises heating the mixture to about 130–150° C.

7. The method of claim 3 wherein the mixture comprises the cellulose fibers and thermobonding agent in ratios by weight of 90:5 to 50:50.

8. The method of claim 7 wherein the mixture comprises 20–40% by weight of thermobonding agent.

9. The method of claim 3 further comprising the step of applying a binder to the web.

10. The method of claim 9 wherein the step of applying a binder to the web comprises saturating the web with the binder and impregnating the binder into the web with pressure on the web.

11. The method of claim 9 wherein the binder is selected from the group consisting of carboxymethyl cellulose, acrylic, styrene butadiene rubber, polyvinyl chloride, polyvinylidine chloride, polyvinyl alcohol and polyvinyl acetate.

12. A method for manufacturing croslinked fibers and converting the crosslinked fibers into a pulp sheet comprising the steps of:
applying a crosslinking substance to a mat of cellulose fibers at a fiber treatment zone;
conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;
separating the cellulose fibers in the fiberizer by hammering them into the fiber output of the substantially unbroken individual cellulose fibers without curing the crosslinking substance; and
thereafter drying and then curing the crosslinking substance to crosslink the individual cellulose fibers and adding the crosslinked fibers to a pulp furnish to form a pulp sheet having increased porosity and impregnability.

13. The method of claim 12 further comprising the step of applying a liquid impregnant to the sheet.

14. The method of claim 13 wherein the applying step comprises applying the crosslinking agent to the sheet.

15. A method for producing crosslinked cellulose fibers, comprising the steps of:
applying a crosslinking substance to a mat of cellulose fibers at a fiber treatment zone;
conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;
separating the cellulose fibers in the fiberizer by hammering them into the fiber output of the substantially unbroken individual cellulose fibers without curing the crosslinking substance;
thereafter drying and then curing the crosslinking substance to crosslink the individual cellulose fibers, and holding the fibers in a retaining station for a selected period of time after drying them.

16. The method of claim 15 wherein the holding step comprises holding the cellulose fibers in a retaining station after curing them.

17. A method for producing crosslinked cellulose fibers, comprising the steps of:
applying a crosslinking substance to a mat of cellulose fibers at a fiber treatment zone;
conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;

separating the cellulose fibers in the fiberizer by hammering them into the fiber output of the substantially unbroken individual cellulose fibers without curing the crosslinking substance; and thereafter drying and then curing the crosslinking substance to crosslink the individual cellulose fibers, wherein the drying step comprises flash drying the separated fibers then introducing them into an expansion chamber.

18. The method of claim 17 wherein the drying step comprises introducing the cellulose fibers into the expansion chamber through a venturi.

19. The method of claim 17 wherein the flash drying step comprises conveying the individual cellulose fibers are conveyed from the fiberizer to the expansion chamber by a conduit that decreases in diameter downstream from the fiberizer to increase a flow velocity of the cellulose fibers before they enter the expansion chamber.

20. A method for producing crosslinked cellulose fibers, comprising the steps of:

applying a crosslinking substance to a mat of cellulose fibers at a fiber treatment zone;

conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;

separating the cellulose fibers in the fiberizer by hammering them into the fiber output of the substantially unbroken individual cellulose fibers without curing the crosslinking substance; and thereafter drying and then curing the crosslinking substance to crosslink the individual cellulose fibers, wherein the crosslinking agent is selected from the group consisting of methylolated urea, methylolated cyclic ureas, lower alkyl substituted cyclic ureas, dihydroxy cyclic ureas, lower alkyl substituted dihydroxy cyclic ureas, methylolated dihydroxy cyclic ureas, and mixtures thereof.

21. A method for producing crosslinked cellulose fibers, comprising the steps of:

applying a crosslinking substance to a mat of cellulose fibers at a fiber treatment zone;

conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;

separating the cellulose fibers in the fiberizer by hammering them into the fiber output of the substantially unbroken individual cellulose fibers without curing the crosslinking substance; and thereafter drying and then curing the crosslinking substance to crosslink the individual cellulose fibers, wherein the pH of the cellulosic fibers remains above about 2 after the crosslinking agent is applied to the mat.

22. The method of claim 21 wherein the pH is within the range of 2–4.

23. The method of claim 22 wherein the pH is within the range of 3–4.

24. A method for producing crosslinked cellulose fibers, comprising the steps of:

applying a crosslinking substance to a mat of cellulose fibers at a fiber treatment zone;

conveying the mat through the fiber treatment zone and directly and immediately into a fiberizer without drying and curing the crosslinking substance, the fiberizer having a fiberizer inlet, wherein the fiberizer provides sufficient hammering force to separate the cellulose fibers of the mat into a fiber output of substantially unbroken individual cellulose fibers having a nit level of no more than about three;

separating the cellulose fibers in the fiberizer by hammering them into the fiber output of the substantially unbroken individual cellulose fibers without curing the crosslinking substance; and thereafter drying and then curing the crosslinking substance to crosslink the individual cellulose fibers, wherein the separating step comprises separating the cellulose fibers in a hammermill comprising:

a housing;

an elongated rotor within the housing and having a longitudinal axis of rotation, the rotor including a plurality of hammers having distal end surfaces sweeping out an effective rotor surface upon rotation of the rotor about the axis of rotation, the distal end surfaces of the individual hammers upon such rotation sweeping separate cylindrical paths with gaps between the paths, the gaps between the paths not exceeding about one-quarter of an inch;

a rotator that rotates the rotor about the axis of rotation to thereby rotate the hammers to provide the effective rotor surface; and the hammermill including at least one inlet through which a fiber mat is delivered to the effective rotor surface for fiberization by the rotating hammers, the housing defining an outlet located at an intermediate position corresponding to an intermediate portion of the effective rotor surface between the ends of the rotor, the outlet extending substantially the entire length of the housing.

* * * * *

UNITED STATES PATENT AND TRADEMARK OFFICE
CERTIFICATE OF CORRECTION

PATENT NO.   : 6,436,231 B1
DATED        : August 20, 2002
INVENTOR(S)  : Peter A. Graef et al.

It is certified that error appears in the above-identified patent and that said Letters Patent is hereby corrected as shown below:

<u>Title page,</u>
Item [73], Assignee should read: -- Weyerhaeuser Company --

Signed and Sealed this

Eleventh Day of February, 2003

JAMES E. ROGAN
*Director of the United States Patent and Trademark Office*